(12) United States Patent
Casper et al.

(10) Patent No.: US 7,748,845 B2
(45) Date of Patent: Jul. 6, 2010

(54) METHOD AND DEVICE FOR PREVENTING ALTERATIONS IN CIRCADIAN RHYTHM

(76) Inventors: Robert Casper, 89 Crescent Road, Toronto, Ontario (CA) M4W 1T7; Jennifer Wardrop, 150 Bloor Street West, Second Floor, Toronto, Ontario (CA) M5S 2X9; Jonathan Spilkin, c/o University Optometric Clinic 700 University Ave, Medical Suite 3, Toronto, Ontario (CA) M5S 1Z5; Peter Solo, c/o University Optometric Clinic 700 University Ave, Medical Suite 3, Toronto, Ontario (CA) M5S 1Z5; Shadab Rahman, 4795 Bloomburg Drive, Mississauga, Ontario (CA) L5M 7K4

( * ) Notice: Subject to any disclaimer, the term of this patent is extended or adjusted under 35 U.S.C. 154(b) by 22 days.

(21) Appl. No.: 11/833,072

(22) Filed: Aug. 2, 2007

(65) Prior Publication Data
US 2008/0065177 A1 Mar. 13, 2008

Related U.S. Application Data

(63) Continuation-in-part of application No. 10/525,958, filed on Oct. 20, 2005, now Pat. No. 7,520,607.

(60) Provisional application No. 60/406,306, filed on Aug. 28, 2002.

(51) Int. Cl.
*G02C 7/10* (2006.01)
*A61B 5/04* (2006.01)

(52) U.S. Cl. ........................ 351/163; 600/545

(58) Field of Classification Search ................... 351/163
See application file for complete search history.

(56) References Cited

U.S. PATENT DOCUMENTS

| 1,971,941 | A | 8/1934 | Pirani |
| 3,112,886 | A | 12/1963 | Kushner |
| 3,826,751 | A | 7/1974 | Laliberte |
| 4,500,810 | A | 2/1985 | Graff |
| 4,719,248 | A | 1/1988 | Bambury et al. |
| 4,878,748 | A | 11/1989 | Johansen et al. |

(Continued)

FOREIGN PATENT DOCUMENTS

| DE | 197 29 719 A1 | 2/1998 |
| EP | 1 285 676 A2 | 2/2003 |

OTHER PUBLICATIONS

Akerstedt, T. et al., "Alertness-enhancing drugs as a countermeasure to fatigue in irregular work hours", *Chronobiol Int*, 1997, vol. 14, pp. 145-158.

Arai, Y. et al., "Critical exposure time for androgenization of the developing hypothalamus in the female rat", *Endocrinology*, vol. 82, pp. 1010-1014, 1968.

(Continued)

*Primary Examiner*—Scott J Sugarman
*Assistant Examiner*—Dawayne A Pinkney
(74) *Attorney, Agent, or Firm*—Crowell & Moring LLP

(57) ABSTRACT

A method of maintaining circadian rhythm of a subject comprising selectively substantially blocking retinal exposure of the subject to light having a wavelength shorter than a specified wavelength during the night, and an apparatus for carrying out the claimed method comprising an optical filter that selectively at least substantially blocks light having a wavelength shorter than the specified wavelength.

71 Claims, 11 Drawing Sheets

U.S. PATENT DOCUMENTS

| | | | |
|---|---|---|---|
| 4,952,046 | A | 8/1990 | Stephens et al. |
| 5,083,858 | A | 1/1992 | Girerd |
| 5,177,509 | A | 1/1993 | Johansen et al. |
| 5,274,403 | A | 12/1993 | Gott |
| 5,304,212 | A | 4/1994 | Czeisler et al. |
| 5,400,175 | A | 3/1995 | Johansen et al. |
| 5,926,310 | A | 7/1999 | Tamura et al. |
| 6,019,476 | A | 2/2000 | Kirschner |
| 6,156,743 | A | 12/2000 | Whitcomb |
| 6,638,963 | B1 | 10/2003 | Lewy et al. |
| 6,902,296 | B2 | 6/2005 | Searfoss, III |
| 2004/0246437 | A1 | 12/2004 | Ambler et al. |
| 2006/0009822 | A1 | 1/2006 | Savage et al. |
| 2006/0106437 | A1 | 5/2006 | Czeisler et al. |
| 2006/0119954 | A1 | 6/2006 | Casper et al. |

OTHER PUBLICATIONS

Armour, D. et al., "Melatonin in the treatment of insomnia in children and adolescents", *Psychiatric Bulletin*, (2004), vol. 28, pp. 222-224.

Barker, D., "In utero programming of chronic disease" *Clin Sci*, vol. 95, pp. 115-128, 1998.

Barker, D. J. et al., "Fetal nutrition and cardiovascular disease in adult life", *Lancet*, vol. 341, pp. 938-941, 1993.

Barrenetxe, J. et al., "Physiological and metabolic functions of melatonin", J Physiol Biochem., 2004, vol. 60, pp. 61-72.

Benediktsson, R., "Glucocorticoid exposure in utero: new model for adult hypertension", *Lancet*, vol. 341, pp. 339-341, 1993.

Benloucif, S. et al., "Interactions between light and melatonin on the circadian clock of mice", *J Biol Rhythms*, 1999, vol. 14, pp. 281-289.

Benshoff, H. M. et al., "Suppression of pineal melatonin in *Peromyscus leucopus* by different monochromatic wavelengths of visible and near-ultraviolet light (UV-A)", *Brain Res.*, 1987, vol. 420, pp. 397-402.

Blask, D. E. et al., "Melatonin-depleted blood from premenopausal women exposed to light at night stimulates growth of human breast cancer xenografts in nude rats", *Cancer Res.*, 2005, vol. 65, pp. 11174-11184.

Blask, D. E. et al., "Growth and fatty acid metabolism of human breast cancer (MCF-7) xenografts in nude rats: impact of constant light-induced nocturnal melatonin suppression", *Breast Cancer Res Treat.*, 2003, vol. 79, pp. 313-320.

Cajochen, C. et al., "High Sensitivity of Human Melatonin, Alertness, Thermoregulation, and Heart Rate to Short Wavelength Light", *J Clin Endocrinol Metab*, 2005, vol. 90, No. (3), pp. 1311-1316.

Colligan, M. J. et al., "Shiftwork: Effects of social and family life. Shiftwork: Occupational Medicine" State of the Art Reviews, 1990, vol. 5, No. (2), pp. 315-322.

Czeisler, C. A. et al., "Exposure to bright light and darkness to treat physiologic maladaptation to night work", *N. Engl J Med*, 1990, vol. 322, pp. 1253-1259.

Czeisler, C. A. et al.," Bright light induction of strong (type 0) resetting of the human circadian pacemaker", *Science*, 1989, vol. 244, pp. 1328-1333.

Davis, S. et al., "Night shift work, light at night, and risk of breast cancer" *J Nat! Cancer Inst.*, 2001 vol. 93, pp. 1557-1562.

Dawson, D. et al., "Timed exposure to bright light improves sleep and alertness during simulated night shifts", *Sleep*, 1991, vol. 14, pp. 511-516.

Edwards, C. R. et al., "Dysfunction of placental glucocorticoid barrier: a link between the fetal environment and adult hypertension?", *Lancet*, vol. 341, pp. 355-357, 1993.

Frank, A. L., "Injuries related to shiftwork", *Am J Prev Med*, 2000, vol. 18, pp. 33-36.

Gibson, E. S. et al., "The Impact of "Sleepiness" on Adolescent Students" Report of Population Health Grant 5555-15-1997-0000051, Health Canada, 1998-2002.

Gibson, E. S. et al., "'Sleepiness' is serious in adolescence: Two surveys of 3235 Canadian students" *BMC Public Health*, 2006, vol. 6, No. 116, pp. 1-9.

Goland, R. S. et al., "Elevated levels of umbilical cord plasma corticotropin-releasing hormone in growth-retarded fetuses", *J Clin Endocrinol Metab*, vol. 77, pp. 1174-1179, 1993.

Gustafsson, J. A. et al., "Sex steroid induced changes in hepatic enzymes", *Annu Rev Physiol*, vol. 45, pp. 51-60, 1983.

Hammer, F. et al., "Cortisol metabolism in hypertension", *Best Pract Res Clin Endocrinol Metab.*, 2006, vol. 20, pp. 337-353.

Hansen, J., "Light at night, shiftwork, and breast cancer risk", *J Natl Cancer Inst.*, 2001, vol. 93, pp. 1513-1515.

Hattar, S. at al., "Melanopsin and rod—cone photoreceptive systems account for all major accessory visual functions in mice", *Nature*, 2003, vol. 424, pp. 76-81.

Healy, D. et al., "The circadian system and affective disorders: clocks or rhythms?", *Chronobiol Intern*, 1990, vol. 7, pp. 5-9.

Hoddes, E. et al., "Quantification of sleepiness: A new approach", *Psychophysiol*, 1973, vol. 10, pp. 431-436.

Horowitz, T. S. et al., "Efficacy of bright light and sleep/darkness scheduling in alleviating circadian maladaptation to night work" *Am J Physiol Endocrinol Metab*, 2001, vol. 281, pp. E384-E391.

Ishida, A. et al., "Light activates the adrenal gland: Timing of gene expression and glucocorticoid release", Cell Metab., 2005, vol. 2, pp. 297-307 and Comment in: Cell Metab., Nov. 2005, vol. 2, No. (5), pp. 278-281.

Johns, M. A., "A new method for measuring daytime sleepiness: the Epworth Sleepiness Scale", *Sleep*, 1991, vol. 14, pp. 540-545.

Kayumov, L. et al., "A randomized, double-blind, placebo-controlled crossover study of the effect of exogenous melatonin on delayed sleep phase syndrome", Psychosom Med., 2001, vol. 63, pp. 40-48.

Kayumov, L. et al., "Blocking Low-Wavelength Light Prevents Nocturnal Melatonin Suppression with No Adverse Effect on Performance during Simulated Shift Work", *J Clin Endocrinol Metab.*, 2005, vol. 90, pp. 2755-2761.

Kayumov, L. et al, "Melatonin, sleep, and circadian rhythm disorders", *Semin Clin Neuropsychiatry*, 2000, vol. 5, pp. 44-55.

Khalsa, S. B. et al., "A phase response curve to single bright light pulses in human subjects" *J Physiol.*, 2003, vol. 549, pp. 945-952.

Krupp, L. B. et al, "The fatigue severity scale. Application to patients with multiple sclerosis and systemic lupus erythematosus", *Arch. Neurol.*, 1989, vol. 46, pp. 1121-1123.

Kubo, T. et al., "Prospective Cohort Study of the Risk of Prostate Cancer among Rotating-Shift Workers: Findings from the Japan Collaborative Cohort Study", *Am J Epidemiol*, 2006, vol. 164, pp. 549-555.

Kubota, T. et al., "Effects of nocturnal bright light on saliva melatonin, core body temperature and sleep propensity rhythms in human subjects", *Neurosci Res.*, 2002, vol. 42, pp. 115-122.

Lindsay, R. S. at al., "Inhibition of 11-beta-hydroxysteroid dehydrogenase in pregnant rats and the programming of blood pressure in the offspring", *Hypertension*, vol. 27, pp. 1200-1204, 1996.

Lindsay, R. S. et al., "Prenatal glucocorticoid exposure leads to offspring hyperglycaemia in the rat: studies with the 11 β-hydroxysteroid dehydrogenase inhibitor carbenoxolone", *Diabetologia*, vol. 39, pp. 1299-1305, 1996.

Luna, T. D., "Air Traffic Controller Shiftwork: what are the implications for aviation safety? a review", *Aviat Space Environ Med*, 1997, vol. 68, pp. 69-79.

Mitler, M. M. et al., "Catastrophes, Sleep, and Public Policy: Consensus Report", *Sleep*, 1988, vol. 11, pp. 100-109.

Newnham, J. P. et al., "Maternal, but not fetal, administration of corticosteroids restricts fetal growth", *J Matern Fetal Med*, vol. 8, pp. 81-87, 1999.

Nowak, J. Z. et al., "Melatonin and its physiological and therapeutic properties", *Pharmacy World & Science*, vol. 20, No. 1, pp. 18-27, 1998.

Nyirenda, M. J. et al., "Glucocorticoid exposure in late gestation permanently programs rat hepatic phosphoenolpyruvate carboxykinase and glucocorticoid receptor expression and causes glucose intolerance in adult offspring", *J Clin Invest*, vol. 15, pp. 2174-2181, 1998.

Okawa, M. et al., "Circadian rhythm sleep disorders in adolescents: clinical trials of combined treatments based on chronobiology", *Psychiatry Clin Neuroscl.*, 1998, vol. 52, pp. 483-490.

Owens, J., "Insomnia in Children and Adolescents", *Journal of Clinical Sleep Medicine*, 2005, vol. 1, pp. 454-e458.

Panda, S. et al., "Coordinated transcription of key pathways in the mouse by the circadian clock", *Cell*, 2002, vol. 109, pp. 307-320.

Perreau-Lenz, S. et al., "The Biological Clock: The Bodyguard of Temporal Homeostasis", *Chronobiology International*, 2004, vol. 21, No. 1, pp. 1-25.

Phelps, J., "Dark therapy for bipolar disorder using amber lenses for blue light blockade", *Med Hypotheses*, 2008, vol. 70, pp. 224-229.

Reinisch, J. M. et al., "Prenatal exposure to prednisone in humans and animals retards intrauterine growth", *Science*, vol. 202, pp. 436-438, 1978.

Revell, V. et al., "Alerting effects of light are sensitive to very short wavelengths", *Neuroscience Letters*, 2006, vol. 399, pp. 96-100.

Richter, H. G. et al., "The Circadian Timing System: Making Sense of day/night gene expression", 2004, *Biol Res*, vol. 37, pp. 11-28.

Rosa, R. R. et al., Intervention factors for promoting adjustment to nightwork and shiftwork. *Occup Med* 1995 5: 391-414.

Runnebaum, I. B. et al., "Glucocorticoids inhibit Cell Death in Ovarian Cancer and Up-regulate Caspase Inhibitor clAP2", *Clin Cancer Res*, 2005, vol. 11, pp. 6325-6332.

Schernhammer, E. S. et al., "Rotating Night Shifts and Risk of Breast Cancer in Women Participating in the Nurses' Health Study", *J Natl Cancer Inst.*, vol. 93, pp. 1563-1568.

Schernhammer, E. S. et al., "Night-shift work and risk of colorectal cancer in the nurses' health study", *J Natl Cancer Inst.*, 2003, vol. 95, pp. 825-828.

Schrey, M. P. et al., "Bombesin and glucocorticoids stimulate human breast cancer cells to produce endothelin, a paracrine mitogen for breast stromal cells", *Cancer Research*, 1992, vol. 52, pp. 1786-1790.

Shanahan, T. L. et al., "Resetting the melatonin rhythm with light in humans", *J Biol Rhythms*, 1997, vol. 12, pp. 556-567.

Shirayama, M. et al., "The psychological aspects of patients with delayed sleep phase syndrome (DSPS)", *Sleep Med.*, 2003, vol. 4, No. (5), pp. 427-433.

Smith, L. et al., "Increased injuries on night shift", *Lancet*, 1994, vol. 344, pp. 1137-1139.

Sookoian, S. et al., "Effects of rotating shift work on biomarkers of metabolic syndrome and inflammation", *J Intern Med*, 2007, vol. 261, pp. 285-292.

Steckler, T. et al., "Glucocorticoids and depression" *Baillieres Best Pract Res Clin Endocrinol Metab.*, 1999, vol. 13, pp. 597-614.

Sunter, D., "Working Shift", Perspectives, Statistics Canada (Catalogue 75-001E), Spring 1993, pp. 16-23.

Thapan, A. et al., "An action spectrum for melatonin suppression: evidence for a novel non-rod, non-cone photoreceptor system in humans", *J Physiol*, 2001, vol. 535, pp. 261-267.

Tuunainen, a. et al., "Depression and endogenous melatonin in post menopausal women", *J Affect Disord.*, 2002, vol. 69, No. (1-3), pp. 149-158.

Van Dongen, H. P., "Shift work and Inter-individual differences in sleep and sleepiness", *Chronobiol Int.*, 2006, vol. 23, pp. 1139-1147.

Van Dongen, P. A. et al., "The cumulative cost of additional wakefulness: dose-response effects on neurobehavioral functions and sleep physiology from chronic sleep restriction and total sleep deprivation", *Sleep*, 2003, vol. 26, pp. 117-126.

Ward, R. M. "Pharmacologic enhancement of fetal lung maturation", *Clin Perinatol*, vol. 21, pp. 523-542, 1994.

Wetterberg, L., "Clinical importance of Melatonin", *Prog Brain Res.*, 1979, vol. 52, pp. 539-4.

Wetterberg, L., "Chapter 3. In: Shaffi M, Shaffi SL, eds. *Melatonin in adult depression*. Washington DC, MD", American Psychiatric Press Inc.; 1998, pp. 43-79.

Whitmore, J. N. et al., "Psychophysiological effects of a brief nocturnal light exposure", *J Hum Ergol.*, 2001, vol. 30, pp. 267-272.

Wirz-Justice, A. "Biological rhythm disturbances in mood disorders", *Int Clin Psychopharmacol.*, 2006, vol. 21 Suppl 1: S11-5.

Wolfson, A. R. et al., "Early school start times affect sleep and daytime functioning in adolescents", Sleep Research, 1996, vol. 25, pp. 117.

Wolfson, A. R. et al., "Sleep schedules and daytime functioning in adolescents", Child Dev, Aug. 1998, vol. 69, pp. 875-887.

Wood, P. A. et al., "Circadian clock coordinates cancer cell cycle progression, thymidylate synthase, and 5-fluorouracil therapeutic index", *Mol Cancer Ther.*, 2006, vol. 5, pp. 2023-2033.

Zeitzer, J. M. et al., "Sensitivity of the human circadian pacemaker to nocturnal light: melatonin phase resetting and suppression", *J Physiol.*, 2002, vol. 526, pp. 695-702.

Horne, J. A. et al., "A Self-Assessment Questionnaire to Determine Morningness-Eveningness in Human Circadian Rhythms", International Journal of Chronobiology, Jun. 1976, pp. 97-110, vol. 4, Gordon and Breach, Science Publishers Ltd.

Gooneratne, N. S. et al., "The Validity and Feasibility of Saliva Melatonin Assessment in the Elderly", Journal of Pineal Research, 2003, pp. 88-94, vol. 34, Blackwell Munksgaard.

Lewy, A. J. et al., "The Endogenous Melatonin Profile as a Marker for Circadian Phase Position", Journal of Biological Rhythms, Jun. 1999, pp. 227-236, vol. 14, No. 3, Sage Publications, Inc.

Bergmann, M. W., "Recovery After Sleep Deprivation in SCN-Lesioned Rats", Sleep, 2002, pp. A184-A186, vol. 25, American Academy of Sleep Medicine.

Beniashvili, D. S. et al., "Effect of Light/Dark Regimen on N-Nitrosoethylurea-Induced Transplacental Carcinogensis in Rats", Cancer Letters 163, (2001), pp. 51-57, Elsevier Science Ireland Ltd., PII: S0304-3835(00)00673-X.

Hahn, R. A.,"Profound Bilateral Blindness and the Incidence of Breast Cancer", Epidemiology Resources Inc., 1991, pp. 208-210, vol. 2.

Kawachi, MD., I. et al., "Prospective Study of Shift Work and Risk of Coronary Heart Disease in Women", Circulation, 1995, pp. 3178-3182, vol. 92, The American Heart Association, Inc.

Hansen, J., "Increased Breast Cancer Risk Among Women Who Work Predominantly at Night", Epidemiology, 2001, pp. 74-77, vol. 12, No. 1, Lippincott Williams & Wilkins, Inc.

Honma, S. et al., "Light Suppression of Nocturnal Pineal and Plasma Melatonin in Rats Depends on Wavelength and Time of Day", Neuorscience Letters, (1992), pp. 201-204, vol. 147, Elsevier Scientific Publishers Ireland, Ltd.

Tynes, T. et al., "Incidence of Breast Cancer in Norwegian Female Radio and Telegraph Operators", Cancer Causes and Control, 1996, pp. 197-204, vol. 7, Rapid Science Publishers.

Cardinali, D. P. et al., "Melaton in Sleep Disorders and Jet-Lag", NeuorendocrInology Letters, 2002, pp. 9-13, vol. 23, ISSN 0172-7801.

Brainard, et al., "The Influence of Different Light Spectra on the Suppression of Pineal Melatonin Content in the Syrian Hamster, Department of Anatomy," Brain Research, 294 (1984) 333-339, Elsevier Science Publishers B.V., 1984.

Zeitzer, et al., "Photopic Tranduction Implicated in Human Circadian Entrainment," Neuroscience Letters 232 (1997) 135-183.

Wright, H. R. et al., "Effect of Light Wavelengnth on Suppression and Phase Delay of the Melatonin Rhythm", Chronobiology International, vol. 18, No. 5, 2001, pp. 801-808.

European Search Report dated Jun. 30, 2006 (Five (5) pages).

European Search Report dated Oct. 12, 2005 (Five (5) pages).

International Search Report dated Dec. 16, 2003 (Three (3) pages).

International Search Report dated Apr. 29, 2008 (Four (4) pages).

Written Opinion of The International Searching Authority dated Apr. 29, 2008 (Nine (9) pages).

Minutes of Oral Proceedings of EP 03 790 601.3.

Summons to Attend Oral Proceedings of EP 03 790 601.3.

METHOD AND DEVICE FOR PREVENTING ALTERATIONS IN CIRCADIAN RHYTHM

CROSS REFERENCE TO RELATED APPLICATIONS

This application is a continuation-in-part of co-pending U.S. patent application Ser. No. 10/525,958, which is the US national stage of international application no. PCT/CA03/001324, filed Aug. 28, 2003. Priority is claimed based on U.S. provisional patent application No. 60/406,306, filed Aug. 28, 2002.

FIELD OF THE INVENTION

The present invention relates to methods and devices for maintaining circadian rhythm in a subject. The present invention further relates to normalizing gene expression levels of genes that exhibit a circadian rhythm expression pattern in a subject exposed to light at night. The present invention further relates to normalizing levels of melatonin and glucocorticoids in a subject exposed to light at night.

BACKGROUND OF THE INVENTION

Approximately 25% of the workforce in North America is involved in work outside the usual daytime hours.[1] Previous work has shown that night shift work, especially rotating shift work can have detrimental affects both in the short term and long term compared to day shift work. In the short term there is an increased incidence of accidents and impaired job performance due to reduced alertness,[2-6] while in the long term there is an increased risk of various forms of cancer including breast, prostate and colorectal carcinoma.[7-10] Higher incidence of obesity, cardiac disease and stress related psychosomatic disorders have also been noted in these chronic rotating shift workers.[11-13] These adverse health effects are strongly connected to circadian rhythm disruption due to bright light exposure at night. Circadian rhythms exhibit roughly a 24 hour pattern and are observed in various physiological functions including, but not limited to, sleep/wake cycle, feeding times, mood, alertness, cell proliferation and even gene expression in various tissue types.[14-16] These rhythms are regulated by the master circadian clock located in the Suprachiasmatic Nuclei (SCN). One key regulator used by the SCN is the neurohormone melatonin, often referred to as the hormone of darkness.[17]

Melatonin (N-acetyl-5-methoxytryptamine) is the principal hormone of the pineal gland, and mediates many biological functions, particularly the timing of those physiological functions that are controlled by the duration of light and darkness. Melatonin is synthesized from tryptophan through serotonin, which is N-acetylated by the enzyme n-acetyl transferase or NAT, and then methylated by hydroxyindol-O-methyl transferase. The enzyme NAT is the rate-limiting enzyme for the synthesis of melatonin, and is increased by norepinephrine at the sympathetic nerve endings in the pineal gland. Norepinephrine is released at night or in the dark phase from these nerve endings. Thus, melatonin secretion is controlled mainly by light and dark phases.

Melatonin is secreted from the pineal gland in a diurnal rhythm, peaking at night and its secretion is highly light sensitive. Nocturnal light exposure significantly suppresses melatonin secretion.[18-20] Interestingly, the suppressive effect of light on melatonin varies with differing wavelengths, and light of relatively short wavelengths (between 420 to 520 nm) has the most pronounced suppressant effect.[21-27] Melatonin has been shown to have various functions such as chronobiotic regulation, immunomodulation, antioxidant effects, regulation of the timing of seasonal breeding and oncostatic effects.[28-30] The oncostatic effects of melatonin have been shown in vitro, and in animal studies showing that constant exposure to light significantly promotes carcinogenesis due to melatonin suppression.[29,30] Hence, melatonin suppression by nocturnal bright light has been proposed as a key mediator of the adverse affects of rotating shift work.

Furthermore, light at night disrupts many other endocrine networks, most notably glucocorticoids.[31] Glucocorticoids are a class of steroid hormone produced in the cortex of the adrenal glands. Cortisol is the most important human glucocorticoid and is associated with a variety of cardiovascular, metabolic, immunologic, and homeostatic functions. Elevated levels of cortisol are associated with a stress response. Light induces gene expression in the adrenal gland via the SCN-sympathetic nervous system and this gene expression is associated with elevated plasma and brain glucocorticoids. The amount of cortisol present in the serum generally undergoes diurnal variation, with the highest levels present in the early morning, and the lowest levels at night. The magnitude of glucocorticoid release by light is also dose dependently correlated with the light intensity. Light-induced clock-dependent secretion of glucocorticoids may serve an adaptive function to adjust cellular metabolism to the light in a night environment, but also illustrates the presence of stress in response to nocturnal lighting. Elevated glucocorticoids pose numerous health risks including hypertension,[32] psychiatric disorders,[33] elevated blood sugar levels, and suppression of the immune system. Increased glucocorticoid levels have also been linked with faster proliferation rates of various carcinomas, most notably breast cancer.[34,35] Elevated levels of cortisol during pregnancy are further associated with metabolic syndrome in offspring. Epidemiological studies in diverse populations have demonstrated an association between low birth weight and the subsequent development of hypertension, insulin resistance, Type 2 diabetes, and cardiovascular disease.[36] This association appears to be independent of classical adult lifestyle risk factors.[37] In explanation, it has been proposed that a stimulus or insult acting during critical periods of growth and development permanently alters tissue structure and function, a phenomenon termed "fetal programming". Intriguingly, there is evidence that this phenomenon is not limited to the first-generation offspring and programming effects may persist in subsequent generations. Epidemiological studies in humans suggest intergenerational effects on birth weight, cardiovascular risk factors, and Type 2 diabetes. Similarly, transgenerational effects on birth weight, glucose tolerance, blood pressure, and the hypothalamic-pituitary-adrenal axis have been reported in animal models. One major hypothesis to explain fetal programming invokes overexposure of the fetus to glucocorticoids.[38] Glucocorticoids exert long-term organizational effects and regulate organ development and maturation.[39,40] In fact, glucocorticoids are exploited therapeutically in the perinatal period to alter the rate of maturation of organs such as the lung.[41] Glucocorticoid treatment during pregnancy reduces birth weight in animals and humans.[42,43] Furthermore, cortisol levels are increased in human fetuses with intrauterine growth retardation or in pregnancies complicated by preeclampsia, which may reflect a stress response in the fetus.[44] It has been shown that rats exposed to dexamethasone (synthetic glucocorticoid) during the last third of pregnancy, are of low birth weight and develop hypertension and glucose intolerance in adulthood.[45-48]

The chronobiotic properties of melatonin can synchronize overall circadian rhythms. In the absence of melatonin there can be desynchronization of the biological clock because the phase or timing of physiological processes does not align with external time queues. Such an example is the markedly delayed time of sleep onset and offset in patients with Delayed Sleep Phase Syndrome (DSPS), which does not correspond to habitual hours of sleep and activity. These individuals exhibit poor alertness and psychomotor performance when they are made to conform to conventional times of activity. Furthermore, such underlying circadian rhythm misalignment can often manifest itself as overt psychological disorders ranging from subsyndromal depression to major depression.

The presence of depression in DSPS populations has been previously reported.[49] DSPS is characterised by sleep onset insomnia where the patient may spend long hours before being able to fall asleep. It is a Circadian Rhythm Sleep Disorder, caused by a desynchronized central biological clock. It has been reported that DSPS patients showed emotional features such as low self esteem, nervousness and lack of control of emotional expression. These characteristics may worsen social withdrawal, causing a loss of social cues in synchronizing their circadian rhythm. Thus, the phase shift becomes more profound and a vicious circle continues.

Apart from psychological disorders in individuals with circadian rhythm misalignment, the presence of depression has also been noted in low melatonin secretors. Wetterberg[50] postulated that low melatonin secretion can be a biological marker for susceptibility to endogenous depression. The clinical symptoms of depressed mood seen in his patients included insomnia, psychomotor retardation, poor memory and concentration and suicidal thoughts. Several studies undertaken in recent years have also shown that both the amplitude and rhythm of melatonin secretion is altered in patients suffering from unipolar depression as well as in patients suffering from bipolar affective disorders.[51,52]

Such rhythm disturbances and associated pathologies are of major concern not only in adults but in adolescents too.[53] Given their post-pubescent hormonal system that is constantly changing along with multi-faceted social demands and poor sleep hygiene, circadian rhythm disruptions can pose as a significant threat to their overall well being.[54] Although limited in numbers, epidemiological and clinical research of sleep in adolescents shows alarming trends. A major study showed that adolescents need 8.5-9.25 hours sleep per night.[55] The same researchers, in a survey of 3,120 high school students, found those who reported grades as C, D or F had 25 minutes less sleep on week nights than those reporting A or B grades.[56] A survey of 3,400 high school students in Ontario, Canada showed that 47.3% of students had less than 8 hours sleep on week nights and 60-70% reported that they were often very sleepy between 8-10 A.M., raising concern about school start time and academic scheduling.[57] The same study found a positive linear relationship between increased daytime "sleepiness" and decreased academic and extracurricular performance. These findings indicate a potentially significant health problem and impact on educational achievement. The survey results suggest that of the approximately 2 million Canadians aged 14-18, there could be as many as 115,000 adolescents with unrecognized medical sleep disorders and at least 975,000 with significant sleep deprivation; a major portion of these sleep disorders can be attributed to circadian rhythm disruption.[57] These findings stress the need for rectifying circadian rhythm misalignment in adolescents to help these young individuals in achieving their full potential.

Exposure to bright light at night can desynchronize the SCN, the master circadian clock leading to the mistiming of various physiological functions resulting in poor health.

One of the major approaches taken to improve conditions associated with disruption of the usual light-dark cycle include entrainment of the circadian rhythm to a delayed phase using bright light therapy in the hopes of increasing alertness at night and inducing sleep during morning hours.[58-61] However, at the end of the night shift exposure to bright daylight serves as a potent Zeitgeber, overriding the potentially beneficial effects of bright light interventions and negating circadian rhythm entrainment.[62] Additionally, bright light administered at night disrupts the body's natural circadian melatonin profile by preventing the melatonin secretion at night. Substantial research evidence is emerging to implicate potential long term consequences of shift-work associated risk factors including increased risk of cancer, cardiovascular disease, gastrointestinal disorders and mood disorders and their associated morbidity and mortality. Recent studies implicate melatonin secretion disruption with these risk factors.

As an example of one of these known approaches, U.S. Pat. No. 5,304,212 to Czeisler et al. teaches a method for modifying the endogenous circadian pacemaker involving the timed application of light.

U.S. Pat. No. 6,638,963 to Lewy et al. teaches a method for treating circadian rhythm disorders including shift work-related desynchronies that involves the administration of melatonin, melatonin agonists or compounds that stimulate endogenous melatonin production. This type of pharmaceutical based intervention is inevitably associated with compliance problems (including problems related to financial difficulties) and side effect risks.

Most steroid-type hormones have a short half-life, so a large dose or multiple doses would be required to mimic the normal nocturnal rise in a subject. The appropriate dose for this type of pharmaceutical intervention is not known and there is the possibility of side effects or unknown toxicity depending on the purity of the melatonin product used.

U.S. Pat. No. 6,156,743 to Whitcomb teaches a method of decreasing fatigue in humans who are shifting their time of wakefulness (e.g. night shift workers) by administering an effective amount of hydrocortisone (i.e. pharmaceutical cortisol.) While administration of hydrocortisone may be associated with short-term relief from fatigue, as discussed above, elevated levels of cortisol are associated with a number of adverse health effects.

United States patent application publication number 2006/0119954 to Casper et al. ("Casper et al."), which has common inventors with the present application, provides a device for inhibiting melatonin suppression by selectively blocking light of wavelength less than 530 nm. This invention is directed to the inhibition of melatonin suppression, but not moderating the expression of other genes that exhibit a circadian rhythm expression pattern. Further, while generally a useful level of colour recognition is obtained with these filters, they may give transmitted images a "yellow hue" and render certain colours difficult to distinguish, in particular: white/grey/yellow and blue/green/black.

A publication by Phelps [Phelps J, Dark therapy for bipolar disorder using amber lenses for blue light blockade, Med Hypotheses (2007)] studies the use of amber safety goggles at night as a possible therapy for sufferers of bipolar disorder. Such goggles transmit a limited amount of light: most likely, less than 50% of all wavelengths of light; and generally block all wavelengths of light less than about 530 nm. Consequently, such goggles limit the ability to distinguish between colours, as described with respect to Casper et al., and are not suitable for many industrial applications. Further, while Phelps suggests that the symptoms of the bipolar sufferers might be improved as a result of circadian rhythm effects, this is speculative and is based on known information in the field and observation of the symptoms of the subjects involved in the study.

U.S. Pat. No. 4,878,748 to Johansen et al. teaches sunglasses for blocking horizontally polarized light and blue light, blocking light between 300 and 549 nm, but also substantially blocking light at all wavelengths: less than 50% of the light at wavelengths above the "blocked" range is transmitted. Johansen et al. does not address the problems associated with disruption of the circadian rhythm suffered by those exposed to light at night. The Johansen et al. inventors are concerned with protecting the retina from damage caused by exposure to high intensity daylight.

There is a need for a simple, effective and inexpensive method to prevent the varied adverse health effects of light exposure at night, without unduly increasing fatigue or reducing alertness.

SUMMARY OF THE INVENTION

In one aspect, the present invention provides a method of maintaining the circadian rhythm of a subject comprising selectively substantially blocking retinal exposure of the subject to light of wavelengths less than about 490 nm during the night.

In another aspect, the present invention provides a method of maintaining the circadian rhythm of a subject comprising selectively substantially blocking retinal exposure of the subject to light of wavelengths less than about 480 nm during the night.

In yet another aspect, the present invention provides a method of maintaining the circadian rhythm of a subject comprising selectively substantially blocking retinal exposure of the subject to light of wavelengths less than about 470 nm during the night.

In yet another aspect, the present invention provides a method of maintaining the circadian rhythm of a subject comprising selectively substantially blocking retinal exposure of the subject to light of wavelengths less than about 460 nm during the night.

In yet another aspect, the present invention provides a method of normalizing levels of melatonin and at least one glucocorticoid in a subject comprising selectively substantially blocking retinal exposure of the subject to light of wavelengths selected from the group consisting of between about 420 nm and about 490 nm; between about 430 nm and about 490 nm; between about 440 nm and about 490 nm; between about 420 nm and about 480 nm; between about 430 nm and about 480 nm; between about 440 nm and about 480 nm; between about 420 nm and about 470 nm; between about 430 nm and about 470 nm; between about 440 nm and about 470 nm; between about 420 nm and about 460 nm; between about 430 nm and about 460 nm; between about 440 nm and about 460 nm; during the night.

In yet another aspect, the present invention provides a device for maintaining the circadian rhythm of a subject exposed to light at night comprising an optical filter that selectively substantially blocks light of wavelengths less than about 490 nm.

In yet another aspect, the present invention provides a device for maintaining the circadian rhythm of a subject exposed to light at night comprising an optical filter that selectively substantially blocks light of wavelengths less than about 480 nm.

In yet another aspect, the present invention provides a device for maintaining the circadian rhythm of a subject exposed to light at night comprising an optical filter that selectively substantially blocks light of wavelengths less than about 470 nm.

In yet another aspect, the present invention provides a device for maintaining the circadian rhythm of a subject exposed to light at night comprising an optical filter that selectively substantially blocks light of wavelengths less than about 460 nm.

In yet another aspect, the present invention provides a device for maintaining the circadian rhythm of a subject exposed to light at night comprising an optical filter that selectively substantially blocks light of wavelengths selected from the group consisting of between about 420 nm and about 490 nm; between about 430 nm and about 490 nm; between about 440 nm and about 490 nm; between about 420 nm and about 480 nm; between about 430 nm and about 480 nm; between about 440 nm and about 480 nm; between about 420 nm and about 470 nm; between about 430 nm and about 470 nm; between about 440 nm and about 470 nm; between about 420 nm and about 460 nm; between about 430 nm and about 460 nm; between about 440 nm and about 460 nm.

DETAILED DESCRIPTION OF THE INVENTION

Figure 1:
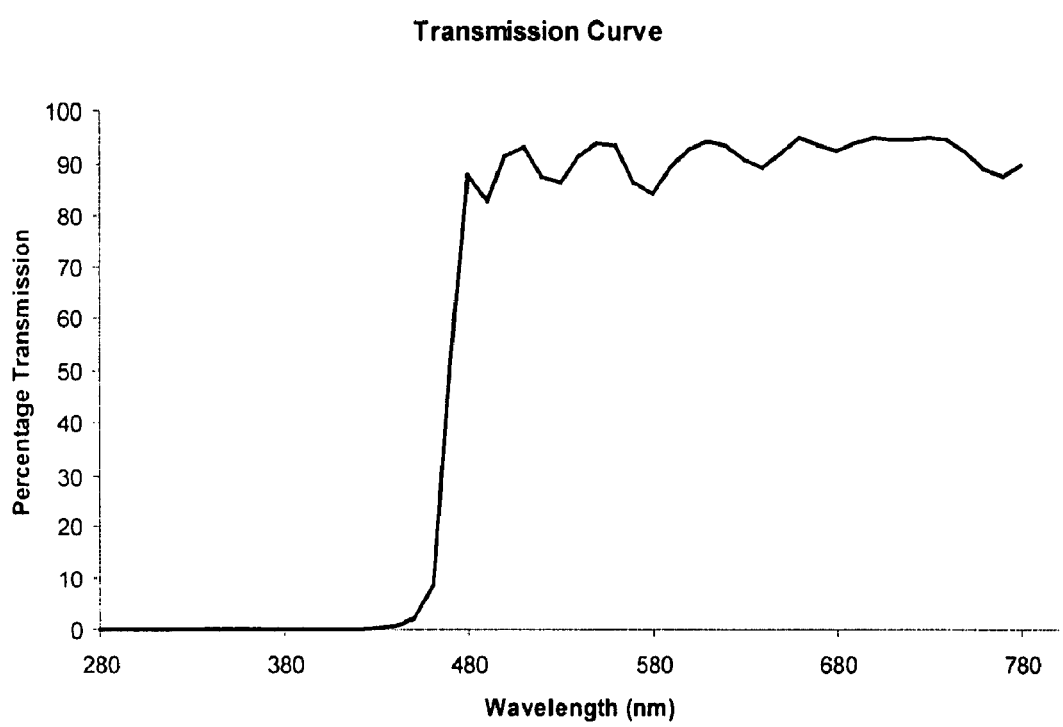
FIG. 1 shows the transmission curve of the lenses of a pair of glasses of one embodiment of the present invention.
Figure 2:
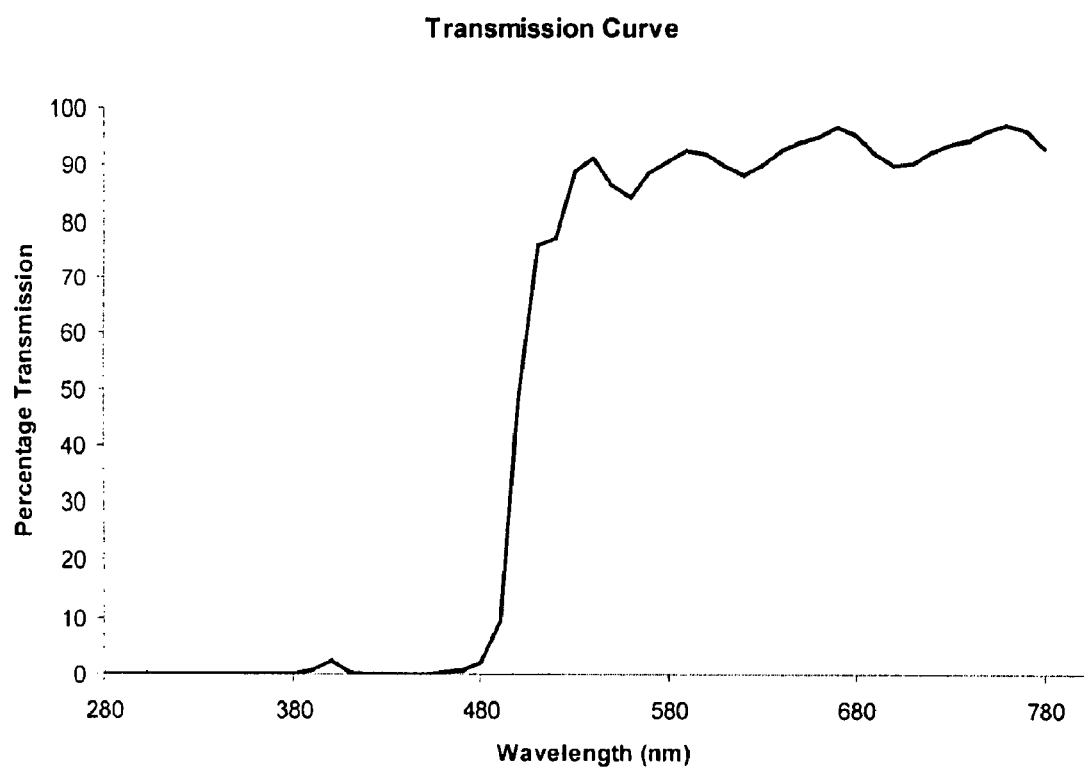
FIG. 2 shows the transmission curve of the lenses of a pair of glasses of another embodiment of the present invention.

The present invention may be accomplished by various means. The following provides a definition for some of the terms used in the specification:

"Circadian rhythm" refers to the cycle of approximately 24 hours in the physiological processes of living organisms. As discussed above, the master circadian clock in mammals is located in the Suprachiasmatic Nuclei (SCN), a group of cells located in the hypothalamus. The SCN receives information about illumination through the eyes. The retina of each eye contains special photoresponsive retinal ganglion cells (RGCs) along with traditional photoresponsive rods and cones. These RGCs contain a photo pigment called melanopsin, and follow a pathway called the retinohypothalamic tract, leading to the SCN. Recently, evidence has emerged that circadian rhythms are found in cells in the body outside the SCN master clock, in other words the expression of genes in various tissues throughout the body also follows a circadian rhythm pattern. In the context of the present invention, a "clock gene" refers to any gene that follows such an expression pattern and is responsible for maintaining circadian oscillations in a specific cellular physiology. It is estimated that about 25% of the human genome shows such a periodicity in expression.

In the context of the present invention, "maintaining the circadian rhythm" of a subject refers to maintaining the amplitude and periodicity of the circadian oscillations observed in physiological processes including, but not limited to, melatonin and cortisol secretion and clock gene expression that would be present in the subject exposed to the geophysical light/dark cycle.

"Normalizing levels" of the expression product of a clock gene refers to either increasing or decreasing the level of expression so as to more closely correspond to the levels of the product that would be found in the same subject exposed to a regular geophysical light/dark cycle. More particularly, with respect to melatonin, it refers to maintaining at least 50% of the level in the same individual kept in darkness.

In the present invention, normalizing the levels of melatonin involves increasing the level of melatonin as compared to the level that would otherwise be present in a subject exposed to light at night. In the context of cortisol, it involves decreasing the level of cortisol as compared to the level that would otherwise be present in a subject exposed to light at night.

In the method of the present invention, the "subject" is a mammal, preferably a human. There may be particular advantages conferred where the subject is a female human subject and even more advantages where the subject is pregnant.

"Substantially blocks" or "substantially blocking", when used in terms of wavelength of light, is defined as transmitting less than 40 percent of the incident wavelengths; less than 30 percent of the incident wavelengths; less than 20 percent of the incident wavelengths; and less than 10 percent of the incident wavelengths. "Selectively blocking" refers to substantially blocking only those wavelengths of light specified, while allowing substantial transmission (i.e. transmission of more than 40 percent; of more than 50 percent; of more than 60 percent; of more than 70 percent; of more than 80 percent; of more than 90 percent; or 100 percent) of the other wavelengths of light in the subject's environment. "About" in the context of wavelength ranges refers to +/−5 nm. In the context of the present invention, an "optical filter" is a device that substantially blocks (as this term is defined above) a range of non-transmitted wavelengths of light. As will be understood by a person of skill in the art, in this context, the term optical filter is not to be understood as equivalent to a colour filter, which, while transmitting light having a certain visual colour may not "substantially block" wavelengths of light outside those of the transmitted visual colour.

"Retinal exposure" refers to light impingement upon the retina of a subject.

"Night" refers to the natural hours of darkness and, more specifically, to the dark phase of the geophysical light/dark cycle. In summer, in peri-equatorial latitudes, this is roughly equivalent to about 2100 hrs (9 pm) to about 0600 hr (6 am), which are the peak hours of melatonin production. "During the night" refers to any time during this period; preferably, the method of the present invention is practiced throughout the night.

"Eyewear" is used as a broad term to encompass such items as eyeglasses, goggles, contact lenses and the like, that are used in connection with the eyes of a user to either shield/protect the eyes from harmful substances, for example chemicals in the context of goggles or to enhance the eyesight of the user, for example contact lenses. It will be understood that the term "eyewear" is not limited to the above examples, and describes any device used in connection with the eyes that contains a viewing window of sorts. Suitably, the eyewear of the present invention is designed to substantially prevent impingement of unfiltered light on the retina of the wearer.

In one embodiment, the invention is a method of maintaining the circadian rhythm of a subject by selectively substantially blocking retinal exposure of the subject to light of wavelengths less than about 490 nm during the night. In another embodiment, the invention is a method of maintaining the circadian rhythm of a subject by selectively substantially blocking retinal exposure of the subject to light of less than about 480 nm; less than about 470 nm; and less than about 460 nm during the night. Optimally, the method is practised throughout the night.

There is some evidence that shorter wavelengths of light in the "blue region" may be associated with increased alertness.[63,64] While the present inventors have not found a significant reduction in alertness associated with substantially blocking all wavelengths below 530 nm, the present invention also includes methods involving more restricted ranges of light blockage and, more specifically, ranges that allow the transmission of certain lower wavelengths of light, outside the key range for maintaining circadian rhythm identified by the inventors.

Thus, in another embodiment, the invention is a method of maintaining the circadian rhythm of a subject by selectively substantially blocking retinal exposure of the subject to light of wavelengths between about 420 nm and about 490 nm; between about 430 nm and about 490 nm; between about 440 nm and about 490 nm; between about 420 nm and about 480 nm; between about 430 nm and about 480 nm; between about 440 nm and about 480 nm; between about 420 nm and about 470 nm; between about 430 nm and about 470 nm; between about 440 nm and about 470 nm; between about 420 nm and about 460 nm; between about 430 nm and about 460 nm; and between about 440 nm and about 460 nm; during the night. Optimally, the method is practised throughout the night. In another embodiment, these specific ranges may be combined with a UV filter to further exclude ultraviolet wavelengths of light.

In one embodiment, the sleep wake cycle of a subject with Delayed Sleep Phase Syndrome (DSPS) can be corrected and maintained. Specifically, a person with DSPS, suffers from sleep onset insomnia and will regularly spend all or a major portion of the night awake and in an artificially lighted environment. Exposure during early night to unfiltered artificial light will expose the subject to low wavelengths that causes the phase delay, shifting the sleep onset to an even later time. By blocking the retinal exposure of the subject to the wavelengths specified above, the phase delays can be attenuated, and the circadian rhythm of the subject can be maintained, thereby mitigating the negative health effects of being awake and in an artificially lighted environment at night and potentially improving sleeping patterns.

In another embodiment, the invention is a method of normalizing levels of melatonin and at least one glucocorticoid, including cortisol, in a subject by selectively substantially blocking retinal exposure of the subject to light of wavelengths less than about 490 nm; less than about 480 nm; less than about 470 nm; and less than about 460 nm during the night. Optimally, the method is employed throughout the night.

In another embodiment, the invention is a method of normalizing levels of melatonin and at least one glucocorticoid, including cortisol, in a subject by selectively substantially blocking retinal exposure of the subject to light of wavelengths between about 420 nm and about 490 nm; between about 430 nm and about 490 nm; between about 440 nm and about 490 nm; between about 420 nm and about 480 nm; between about 430 nm and about 480 nm; between about 440 nm and about 480 nm; between about 420 nm and about 470 nm; between about 430 nm and about 470 nm; between about 440 nm and about 470 nm; between about 420 nm and about 460 nm; between about 430 nm and about 460 nm; and between about 440 nm and about 460 nm; during the night. Optimally, the method is employed throughout the night.

In one embodiment, the invention is a device for maintaining the circadian rhythm of a subject. The device includes an optical filter for selectively substantially blocking light of wavelengths less than about 490 nm; light of wavelengths less than about 480 nm; light of wavelengths less than about 470 nm; and light of wavelengths less than about 460 nm. These optical filters enable good colour recognition and do not impart a significant yellow hue. They also permit an average user to distinguish between most shades of white/grey/yellow and blue/green/black.

In another embodiment, the invention is a device for maintaining the circadian rhythm of a subject that includes an optical filter for selectively blocking light of wavelengths between about 420 nm and about 490 nm; between about 430 nm and about 490 nm; between about 440 nm and about 490 nm; between about 420 nm and about 480 nm; between about 430 nm and about 480 nm; between about 440 nm and about 480 nm; between about 420 nm and about 470 nm; between about 430 nm and about 470 nm; between about 440 nm and about 470 nm; between about 420 nm and about 460 nm; between about 430 nm and about 460 nm; and between about 440 nm and about 460 nm; during the night. These optical filters enable good colour recognition and do not impart a significant yellow hue. They also permit an average user to distinguish between most shades of white/grey/yellow and blue/green/black.

In another embodiment of the invention, an optical filter such as those described above may be applied to the surface of a light source, including an incandescent or fluorescent light bulb. In one embodiment, the optical filter is in the form of a coating.

In another embodiment, a transparent or semi-transparent cover including an optical filter as described above can be releasably attached to a light source to channel the light emitted from the light source through the cover. A light source can include devices that emit light, although this is not their primary function, for example a television screen or a computer monitor. It will be understood by a person skilled in the art that the cover may be any shape or form as long as it is operable to cover the light source that it is to be used with. In an alternative embodiment, the light cover can be permanently attached to a light source.

In another embodiment, the invention is a light source that excludes wavelengths of light less than about 490 nm; less than about 480 nm; less than about 470 nm; or less than about 460 nm; between about 420 nm and about 490 nm; between about 430 nm and about 490 nm; between about 440 nm and about 490 nm; between about 420 nm and about 480 nm; between about 430 nm and about 480 nm; between about 440 nm and about 480 nm; between about 420 nm and about 470 nm; between about 430 nm and about 470 nm; between about 440 nm and about 470 nm; between about 420 nm and about 460 nm; between about 430 nm and about 460 nm; and between about 440 nm and about 460 nm.

In another embodiment, the invention is eyewear that includes an optical filter for blocking light of wavelengths less than about 490 nm; less than about 480 nm; less than about 470 nm; less than about 460 nm; between about 420 nm and about 490 nm; between about 430 nm and about 490 nm; between about 440 nm and about 490 nm; between about 420 nm and about 480 nm; between about 430 nm and about 480 nm; between about 440 nm and about 480 nm; between about 420 nm and about 470 nm; between about 430 nm and about 470 nm; between about 440 nm and about 470 nm; between about 420 nm and about 460 nm; between about 430 nm and about 460 nm; between about 440 nm and about 460 nm. In one embodiment, the optical filter is in the form of a coating.

In Table 1 below, the transmission values of a pair of glasses incorporating polycarbonate lenses vacuum coated with an optical filter made in accordance with the present invention is shown. Wavelengths of light at or below about 460 nm are substantially blocked. These transmission values are shown as a transmission curve in FIG. 1. In Table 2 below, the transmission values of another pair of glasses incorporating polycarbonate lenses vacuum coated with an optical filter made in accordance with the present invention is shown. Here, wavelengths of light at or below about 490 nm are substantially blocked. Both sets of glasses enable good colour recognition, while providing the health benefits of the present invention to those exposed to light at night. These lenses can also be ground according to an optometric prescription to allow vision correction. Table 3 below shows the transmission values of the pair of glasses that substantially blocks light of wavelengths at or below 490 nm with a anti-reflective coating applied thereto.

In one embodiment of the invention, polycarbonate lenses are vacuum coated with a plurality of optical filter layers, which cumulatively provide the selective wavelength blocking of the present invention. In one embodiment, 10 or more layers of optical filter coatings are suitably applied to form lenses of the present invention.

TABLE 1

| Transmission Value | |
|---|---|
| Wavelength nm | Experimental Value |
| 780 | 89.37% |
| 770 | 87.37% |

TABLE 1-continued

| Transmission Value | |
|---|---|
| Wavelength nm | Experimental Value |
| 760 | 88.60% |
| 750 | 91.81% |
| 740 | 94.27% |
| 730 | 94.64% |
| 720 | 94.30% |
| 710 | 94.54% |
| 700 | 94.82% |
| 690 | 93.54% |
| 680 | 92.32% |
| 670 | 93.16% |
| 660 | 94.58% |
| 650 | 92.04% |
| 640 | 89.00% |
| 630 | 90.48% |
| 620 | 93.35% |
| 610 | 93.88% |
| 600 | 92.65% |
| 590 | 89.05% |
| 580 | 84.17% |
| 570 | 86.36% |
| 560 | 93.43% |
| 550 | 93.60% |
| 540 | 91.40% |
| 530 | 86.33% |
| 520 | 87.47% |
| 510 | 93.03% |
| 500 | 91.06% |
| 490 | 82.85% |
| 480 | 87.61% |
| 470 | 51.54% |
| 460 | 8.47% |
| 450 | 1.96% |
| 440 | 0.63% |
| 430 | 0.23% |
| 420 | 0.12% |
| 410 | 0.00% |
| 400 | 0.00% |
| 390 | 0.00% |
| 380 | 0.00% |
| 370 | 0.00% |
| 370 | 0.00% |
| 365 | 0.00% |
| 360 | 0.00% |
| 355 | 0.00% |
| 350 | 0.00% |
| 345 | 0.00% |
| 340 | 0.00% |
| 335 | 0.00% |
| 330 | 0.00% |
| 325 | 0.00% |
| 320 | 0.00% |
| 315 | 0.00% |
| 310 | 0.00% |
| 309 | 0.00% |
| 300 | 0.00% |
| 295 | 0.00% |
| 290 | 0.00% |
| 285 | 0.00% |
| 280 | 0.00% |

TABLE 2

| Transmission Value | |
|---|---|
| Wavelength nm | Experimental Value |
| 780 | 92.76% |
| 770 | 95.85% |
| 760 | 96.80% |
| 750 | 95.84% |

TABLE 2-continued

| Transmission Value | |
|---|---|
| Wavelength nm | Experimental Value |
| 740 | 94.13% |
| 730 | 93.26% |
| 720 | 92.01% |
| 710 | 90.26% |
| 700 | 89.87% |
| 690 | 91.91% |
| 680 | 95.18% |
| 670 | 96.38% |
| 660 | 94.83% |
| 650 | 93.57% |
| 640 | 92.44% |
| 630 | 89.61% |
| 620 | 88.03% |
| 610 | 89.83% |
| 600 | 91.84% |
| 590 | 92.45% |
| 580 | 92.73% |
| 570 | 88.59% |
| 560 | 84.05% |
| 550 | 86.53% |
| 540 | 90.94% |
| 530 | 88.74% |
| 520 | 77.04% |
| 510 | 75.63% |
| 500 | 47.67% |
| 490 | 9.15% |
| 480 | 1.94% |
| 470 | 0.66% |
| 460 | 0.29% |
| 450 | 0.14% |
| 440 | 0.12% |
| 430 | 0.13% |
| 420 | 0.16% |
| 410 | 0.46% |
| 400 | 2.27% |
| 390 | 0.67% |
| 380 | 0.00% |
| 370 | 0.00% |
| 370 | 0.00% |
| 365 | 0.00% |
| 360 | 0.00% |
| 355 | 0.00% |
| 350 | 0.02% |
| 345 | 0.00% |
| 340 | 0.00% |
| 335 | 0.00% |
| 330 | 0.00% |
| 325 | 0.00% |
| 320 | 0.00% |
| 315 | 0.00% |
| 310 | 0.00% |
| 305 | 0.00% |
| 300 | 0.00% |
| 295 | 0.00% |
| 290 | 0.00% |
| 285 | 0.00% |
| 280 | 0.00% |

TABLE 3

| Transmission Value | |
|---|---|
| 780 | 93.43% |
| 770 | 93.27% |
| 760 | 95.09% |
| 750 | 98.11% |
| 740 | 99.85% |
| 730 | 100.06% |
| 720 | 100.09% |
| 710 | 100.30% |
| 700 | 98.05% |

TABLE 3-continued

| Transmission Value | |
|---|---|
| 690 | 94.41% |
| 680 | 93.10% |
| 670 | 96.14% |
| 660 | 100.16% |
| 650 | 101.20% |
| 640 | 100.36% |
| 630 | 98.36% |
| 620 | 93.24% |
| 610 | 89.22% |
| 600 | 91.78% |
| 590 | 96.39% |
| 580 | 97.85% |
| 570 | 97.52% |
| 560 | 91.62% |
| 550 | 90.05% |
| 540 | 96.31% |
| 530 | 96.64% |
| 520 | 90.23% |
| 510 | 88.14% |
| 500 | 91.77% |
| 490 | 30.73% |
| 480 | 4.88% |
| 470 | 1.28% |
| 460 | 0.49% |
| 450 | 0.20% |
| 440 | 0.13% |
| 430 | 0.10% |
| 420 | 0.08% |
| 410 | 0.03% |
| 400 | 0.00% |
| 390 | 0.00% |
| 380 | 0.00% |
| 370 | 0.00% |
| 370 | 0.00% |
| 365 | 0.00% |
| 360 | 0.00% |
| 355 | 0.02% |
| 350 | 0.00% |
| 345 | 0.01% |
| 340 | 0.00% |
| 335 | 0.00% |
| 330 | 0.00% |
| 325 | 0.00% |
| 320 | 0.00% |
| 315 | 0.00% |
| 310 | 0.00% |
| 305 | 0.00% |
| 300 | 0.00% |
| 295 | 0.00% |
| 290 | 0.00% |
| 285 | 0.00% |
| 280 | 0.00% |

EXAMPLE 1

Animals used for all experiments were adult non-breeding male Sprague Dawley rats (Charles River, Montreal, Canada) at 10 weeks of age (350 grams). These animals have been shown to exhibit robust melatonin profiles and since melatonin secretion is modulated by estrogen, female animals were excluded to reduce confounding factors. Prior to all experiments the animals were kept under 12:12 Light:Dark (LD) cycle (7 pm lights out, 7 am lights on, 475 Lux Incandescent lighting in the animal holding room during the light phase) with ad libitum feeding of standard rat chow and water for two weeks for acclimatization and to ensure circadian entrainment. The experiments were then carried out in three phases Phase 1

In the first phase, the baseline melatonin and corticosterone profile under normal 12:12 LD cycle was determined. In rats, corticosterone, rather than cortisol, is the predominant glucocorticoid produced by the adrenal gland. Corticosterone measurements were done as well as melatonin concentrations to determine the degree of stress the animals were exposed to during the different light conditions and to ensure that excess stress did not affect the results. To this end, starting from 8 pm until 8 am four animals were used every four hours for blood and tissue sample collection under darkness using a safe red light lamp (<5 Lux luminosity) and with the aid of night vision goggles. The animals were anesthetized with Isoflurane gas (5% Induction; 3% Maintenance). 5 ml blood was aspirated by cardiac puncture into tuberculin syringes (20 gauge, 1 inch needles) and stored in pre-chilled heparin coated tubes (BD, Canada). Immediately after blood collection, animals were euthanized by decapitation. The brain was harvested for dissection to collect the hypothalamus. The brain was sectioned using an adult rat brain matrix (Ted Pella, USA) into 2 mm sections and subsequently the hypothalamic region was dissected out. Additionally, the liver and adrenals were also collected. All tissue was snap frozen in liquid nitrogen and stored at $-80°$ C. for RNA extraction at a later time. After completing all blood sampling, the blood was spun at 1000 g for 15 mins to extract the plasma which was then stored at $-80°$ C. for melatonin and corticosterone hormone assays at a later time.

Phase 2

In the second phase of the experiment, the melatonin and corticosterone secretion profile in rats exposed to 12:12 LL cycles or continuous lighting was determined. To this end four animals were housed in a specially designed box. The box was 24"×24"×14" and held two regulation size rat cages. The rat cages were modified such that more than 80% of each plastic side was replaced with galvanized steel mesh wire. The dimensions and bedding used were exactly the same as the original cages in which the animals were housed during entrainment. The modification was to ensure that light could enter freely and not be refracted or filtered by the original plastic sides while still ensuring that the animals were kept under regulation holding conditions. Each modified cage housed two non-breeding male animals. Animals were housed in pairs from the beginning of the entrainment period and the same pairs were transferred to their modified holding cages to negate stress caused by exposure to a new animal. The box did not allow external lighting to enter or internal light to escape preventing any potential alterations in light intensity within the holding conditions. The animals were exposed to light from 7 pm to 8 am. Light was fed evenly throughout the box using fiber optic cables running from a fiber optic light source fitted with a 183 watt tungsten halogen bulb generating 500 Lux light intensity at animal eye level. Animals were sacrificed as in the first phase for blood and tissue sampling. Since the box was designed to hold only four animals, one time point was tested per night and experiments were carried out on four consecutive nights.

Phase 3

In the third phase of the experiment, the melatonin and corticosterone secretion profile in rats exposed to 12:12 LL cycles as in Phase 2, but with optically filtered lighting was determined. The animals were kept under the same conditions as in the second phase of the study, but in this case the light was filtered using holographic notch filters (Kaiser Optical Systems, Ann Arbor, Mich.) specially designed to cut out approximately 10-15 nm wavelength bandwidths. Four notch filters were purchased, each designed to cut out 10-15 nm bandwidths covering the range of approximately 440-530 nm. The notch filter was attached to the light source of the box so that the light was filtered before it entered the fiber optic cables to ensure that all fiber optic bundles delivered the same intensity and wavelength of light. The optically filtered light intensity was adjusted using a rheostat to maintain 500 Lux at animal eye level. Since the box was designed to hold only four animals, one time point per filter or combination of filters was tested per night and experiments were carried out on four consecutive nights for each filter as in phase two. All blood and tissue collection was conducted as previously described. Additionally, to ensure that the animals were exposed to the same conditions during each of the three phases, the animals in the first phase were also kept in the specially designed box, but with no light exposure. The 457.9 nm and 476.5 nm holographic notch filters were initially tested, both alone and combined. Upon completion of sample collection from each phase of experimentation, the blood was used to analyze melatonin and corticosterone from plasma. Hormone analysis was done with commercially available ELISA kits, which have been previously validated. The brain tissue was used for Per2 and Bma-2 clock gene expression studies by real time RT-PCR. The results obtained indicated that both melatonin suppression could be prevented and corticosterone levels kept low with the combination of notch filters that blocked the bandwidth of approximately 452-462 nm and 470-480 nm.

Preliminary data from the hormone analysis demonstrated that the 457.9 nm notch filter was not able to prevent melatonin suppression by light whereas the 476.5 nm filter prevented melatonin suppression. The combination of the 457.9 and 476.5 was also excellent in preventing melatonin suppression by light at midnight. In contrast, the 457.9 nm filter was found effective in preventing a rise in corticosterone secretion by light exposure at midnight but the 476.5 nm filter was less effective. The combination of the 457.9 and 476.5 nm filters was also excellent in preventing increased corticosterone secretion by light at midnight. The combination of the 457.9 and 476.5 nm filters on melatonin and corticosterone secretion was therefore tested in rats sacrificed at 8 pm, 12 am, 4 am, and 8 am (four animals at each time point). The combination of the two filters covering a wavelength range from approximately 452-462 nm and 470-480 nm maintained corticosterone and melatonin secretion profiles under constant light exposure identical to the profiles seen when the rats were kept in the dark.

Data from the gene expression studies demonstrated that the combination of the two filters maintained the expression profile of Per2 and Bmal1 clock genes in the hypothalamus under constant light exposure identical to the profiles seen when the rats were kept in the dark. Per2 and Bmal1 expression show a consistent circadian rhythm across different species. Per2 expression peaks during the day and declines gradually through the course of the night in darkness, while Bmal1 expression is antiphase of Per2 expression. Bmal1 starts to increase with the onset of darkness and peaks around 4 am and decreases to basal levels by the end of night. However, Per2 expression is highly sensitive to light and even a brief exposure to light at night can induce strong Per2 expression in the hypothalamus. Since the filters used were capable of blocking this light induced increase in Per2 expression, it suggests that the filters were capable of preventing the light from activating key centers of hypothalamus involved in circadian entrainment. This response could not have been predicted by the use of each of the notch filters alone.

Figure 3:
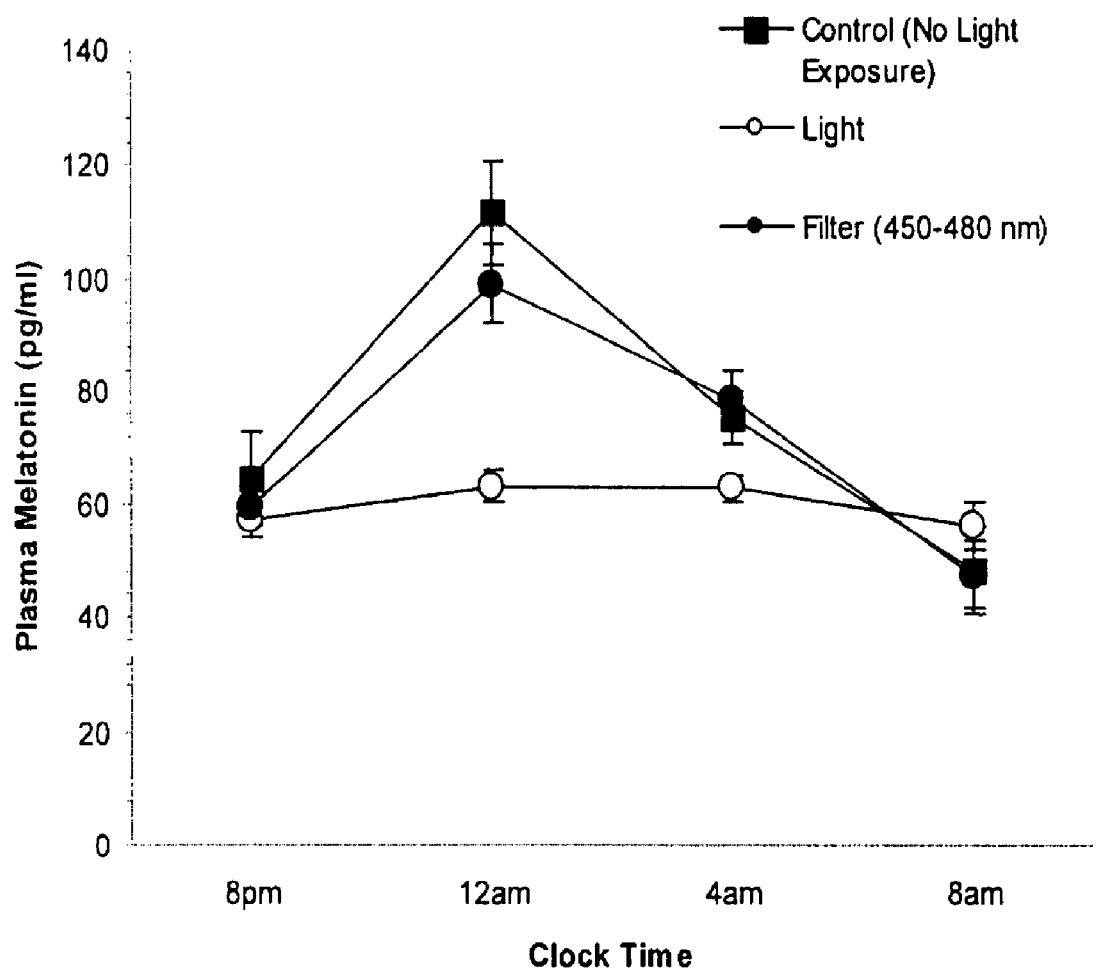
FIG. 3 shows the melatonin profile in an animal model over 12 hours from 8 pm to 8 am in a dark environment, in a light environment and in a lighted environment with a filter of the present invention.
Figure 4:
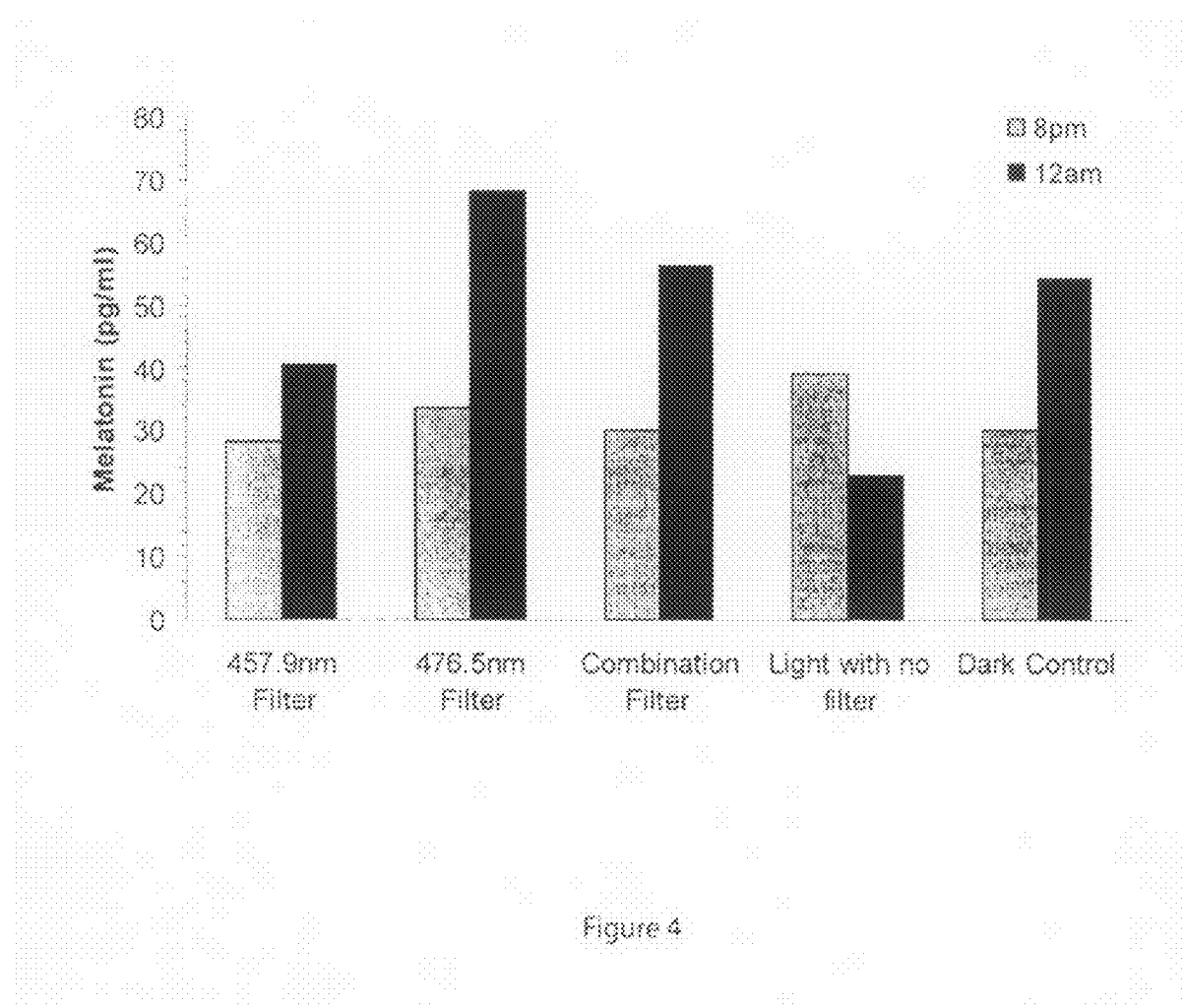
FIG. 4 shows melatonin levels at 8 pm and 12 am in an animal model under lighted conditions with no filter, with a 457.9 nm notch filter, with a 476.5 nm notch filter and with both filters.
Figure 5:
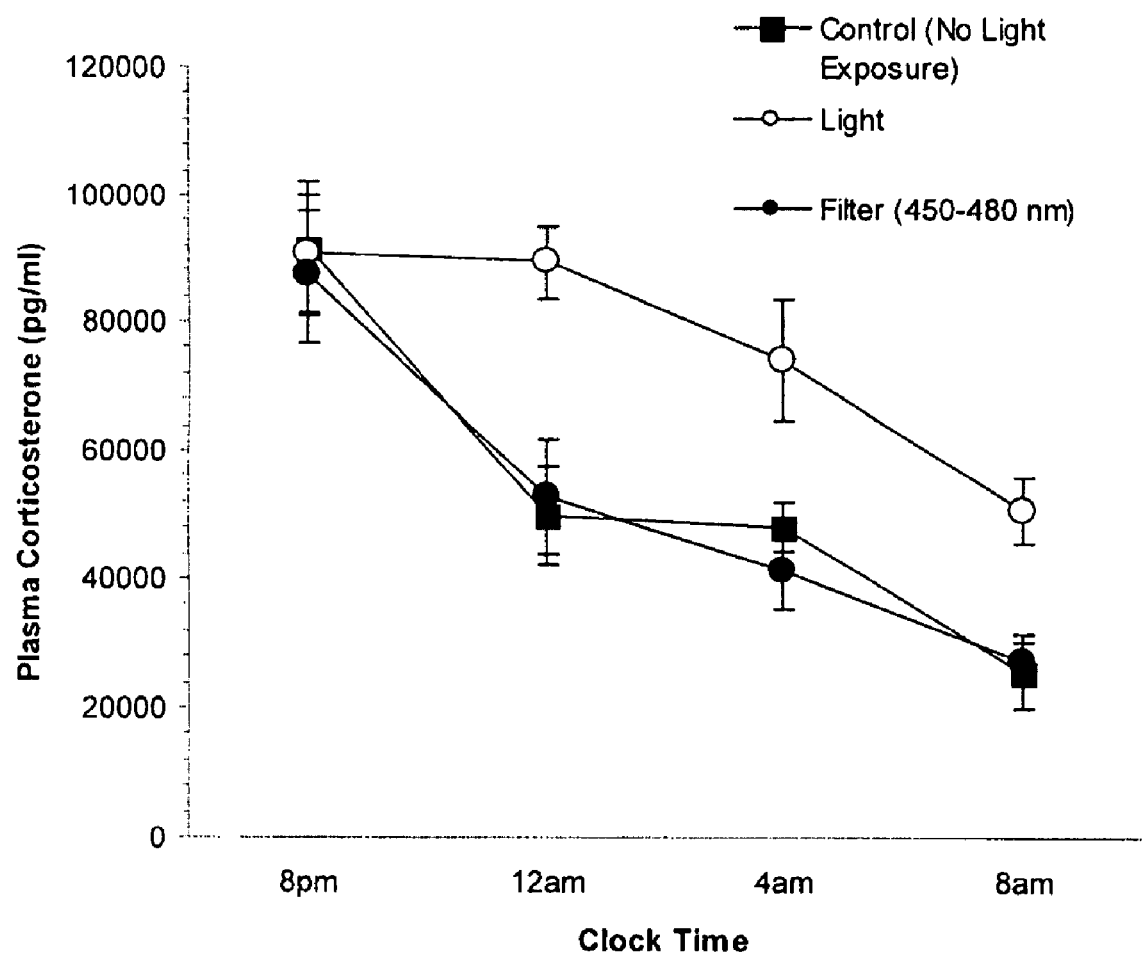
FIG. 5 shows the corticosterone profile in an animal model over 12 hours from 8 pm to 8 am in a dark environment, in a light environment and in a lighted environment with a filter of the present invention.
Figure 6:
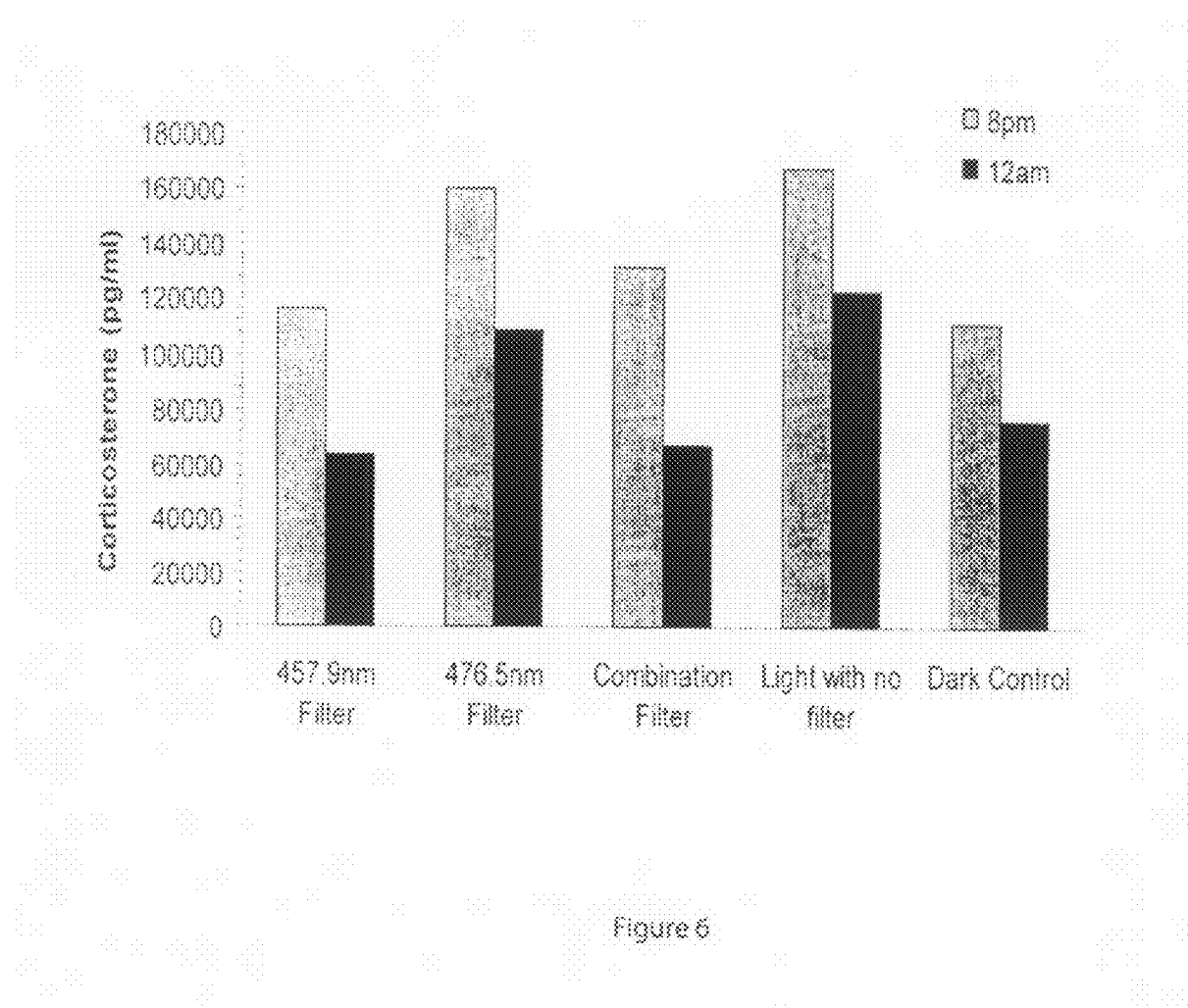
FIG. 6 shows corticosterone levels at 8 pm and 12 am in an animal model under lighted conditions with no filter, with a 457.9 nm notch filter, with a 476.5 nm notch filter and with both filters.
Figure 7:
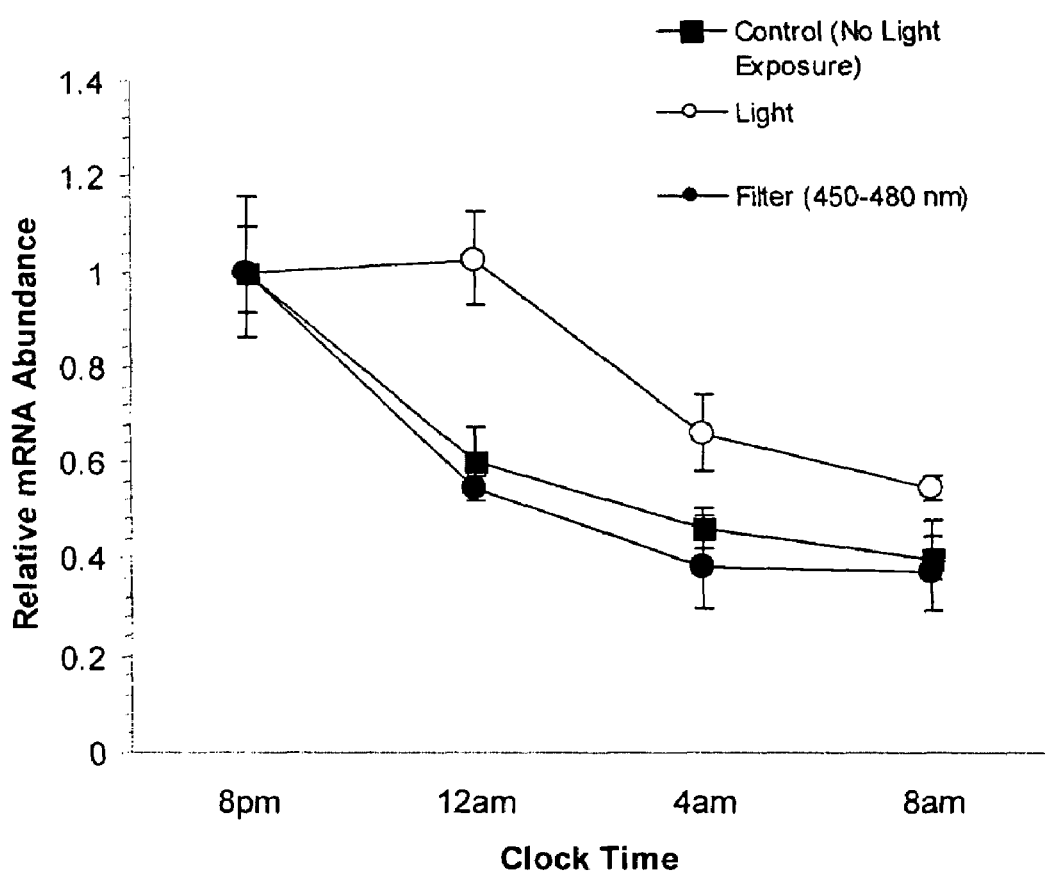
FIG. 7 shows expression of the Per2 clock gene in an animal model over 12 hours from 8 pm to 8 am in a dark environment, in a light environment and in a lighted environment with a filter of the present invention.
Figure 8:
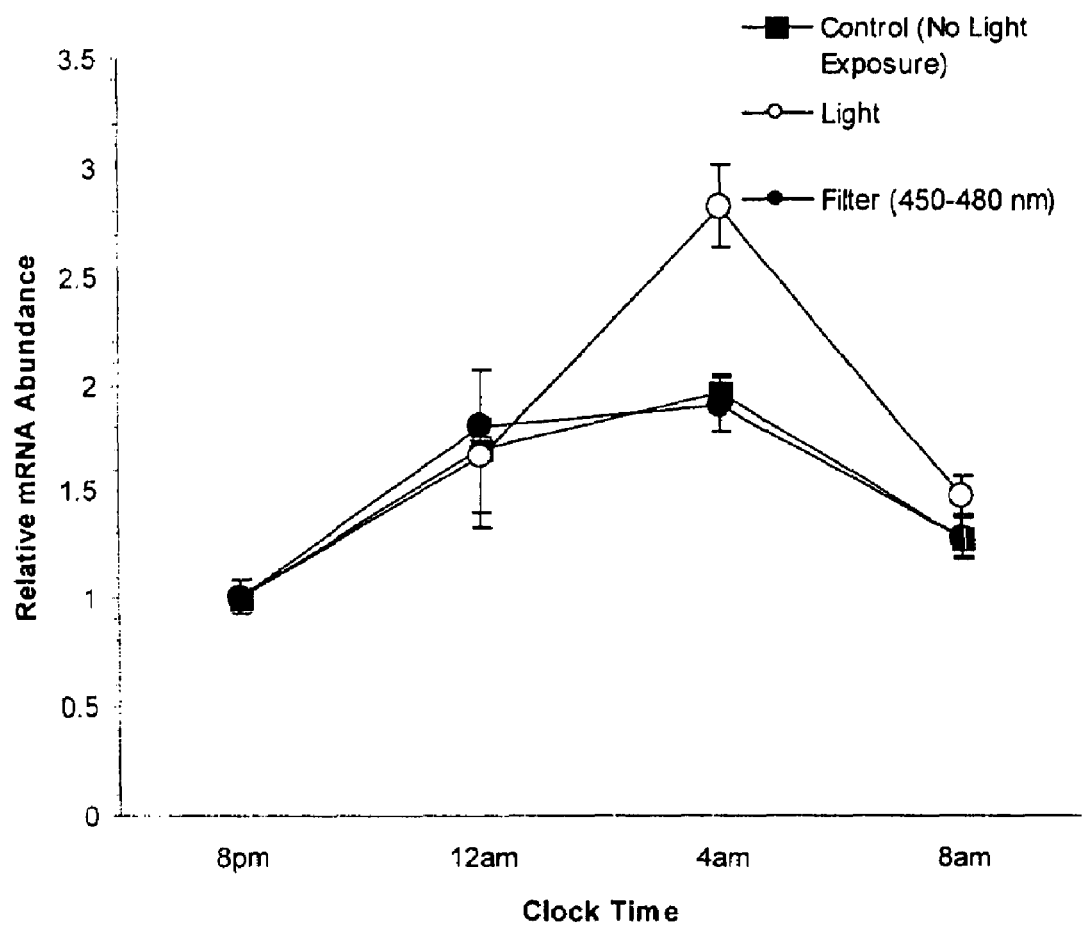
FIG. 8 shows expression of the Bmal1 clock gene in an animal model over 12 hours from 8 pm to 8 am in a dark environment, in a light environment and in a lighted environment with a filter of the present invention.

This data from animal studies shows that filtering this narrow range of low wavelength light (i.e. approximately 450 nm to 480 nm) can normalize melatonin secretion (See FIGS. 3 and 4), reduce glucocorticoid secretion to physiologic levels (See FIGS. 5 and 6) and restore overall circadian rhythm as reflected by normalization of Per2 and Bmal1 (See FIGS. 7 and 8) gene expression in the hypothalamus, even after continuous 12 hour light exposure at night.

It has been demonstrated that specialized goggles containing optical filters that blocked all wavelengths of light below 530 nm, had 73% light transmittance, worked well to restore melatonin profiles in shift workers exposed to bright light conditions (800 Lux). Several alertness and performance tests were conducted using both objective and subjective measures during the nighttime period of exposure to filter light to maintain melatonin secretion.[65] These tests showed that normalized melatonin rhythms do not affect alertness or sleepiness compared to subjects with suppressed melatonin profiles due to bright light while working at night. This evidence assuages concerns that melatonin acts as soporific agent and induces sleepiness and drowsiness.

EXAMPLES 2 TO 3

Based on the results of Example 1, optical filters that block a narrower range of low wavelength light, specifically between 440 nm to 480 nm have been developed. These filters have increased light transmittance and improved color recognition and overall improved visual acuity. As described in Example 1, data from animal studies have shown that filtering this narrow range of low wavelength light can normalize melatonin secretion (FIGS. 3 and 4), reduce glucocorticoid secretion to physiologic levels (FIGS. 5 and 6) and restore overall circadian rhythm as reflected by normalization of Per2 and Bmal1 (FIGS. 7 and 8) gene expression in the hypothalamus, even after continuous 12 hour light exposure at night.

Examples 2 to 3 will test the feasibility of using these filters as goggles in a mock night shift work environment and it is hypothesized that using these filters will restore melatonin secretion and glucocorticoid levels. This is a randomized crossover study with subjects serving as their own controls. Self-report instruments evaluating subjective fatigue, sleepiness and alertness complement the physiological measures of melatonin and cortisol. Subjects are randomly assigned to one of the following crossover study conditions: (1) No light exposure at night; (2) 12 hour bright light (500 Lux) exposure at night; (3) 12 hour filtered bright light (500 Lux) exposure at night; (4) "Mock" filtered (yellow tinted lenses without any melatonin-sensitive light-filtering properties) bright light (500 Lux) exposure to night.

An equal number of healthy male and female subjects will be recruited and consecutively enrolled for a total of 30 subjects. It is anticipated that up to 5 subjects (drop-out rate of 17%) may withdraw before completion. Twenty-five subjects are required to complete this study (see power calculation below). Subjects older than age 45 are not included to avoid any age-related changes in melatonin secretion. Subjects who have prior diagnosis of sleep disorders or major/minor depression are not included since such pathology has been linked to disrupted melatonin rhythms and overall circadian rhythms.[66,67] Active rotating shift workers or individuals with markedly delayed habitual sleep times are not included in the study.

EXAMPLE 2

Measurement of Nocturnal Melatonin and Cortisol Levels Under No Light Baseline Conditions and Under Bright Ambient Light at Night Subjects are randomly assigned to one of the crossover study conditions. The addition of a 'mock' filter arm to the study serves to strengthen the research design, making this a more rigorous, true placebo controlled trial. Subjects are randomly tested under all conditions and the same procedures are carried out for each condition. All study conditions are separated by at least 5 recovery days between the last day of testing for one study condition and the first night of testing for the following condition. Each study condition involves one night of testing. During the night of testing the subjects are asked to remain awake for 12 hours mimicking a 12-hour night shift from 1900 h to 0700 h. Starting from 1900 h, saliva samples are collected from the subjects at an hourly interval until 0700 h giving a total of 13 samples per subject per experimental condition. During the testing period the subjects receive two short meal breaks at 4 hours (2300 h) and 8 hours (0300 h) after the start of the session but are asked to refrain from eating or drinking (other than water) throughout the remainder of the time as food residues can contaminate the saliva samples. The saliva samples are used for hormone analysis using commercially available ELISA kits for melatonin (ALPCO, USA) and cortisol (Cayman Chemical, USA).

Staying awake the whole night under darkness for establishing baseline conditions may prove to be difficult, as a result, a dim red light (<5 Lux) will be used at all times. Dim red light, at less than 5 Lux intensity has been shown to not suppress melatonin secretion.[65] Furthermore, the subjects will be completing psychometric questionnaires every two hours, which will reduce their period of inactivity.

It is anticipated that the experimental filters will be effective in preventing melatonin suppression and reducing stress levels induced by nocturnal bright light exposure as observed in our preliminary in vivo studies. Furthermore, the mock filters will not preserve the physiologic melatonin levels or reduce stress levels in response to nocturnal bright light exposure.

EXAMPLE 3

Evaluation of Subjective Fatigue, Sleepiness and Alertness Under No Light Baseline Conditions and Under Bright Ambient Light at Night As in Example 2, subjects are randomly assigned to one of the crossover study conditions. These tests are carried out on the same night of testing as Example 2. Subjects are asked to complete state questionnaires half-hour after the start of the session and at 2-hourly intervals thereafter to assess changes in sleepiness and fatigue throughout the night. The subjects will have the aid of a dim red light (<5 Lux) to complete the forms and the forms will be printed in large font in order to aid in reading under dim light conditions. Subjective sleepiness will be assessed using the Stanford Sleepiness Scale (SSS)[68], subjective fatigue will be measured using the Fatigue Severity Scale (FSS)[69] and alertness will be measured using the Alertness Scale (AS)[70]. For the SSS subjects are asked to choose one of several statements that best describes their current level of sleepiness (SSS), ranging from being wide awake to almost in a reverie. For the AS the subjects choose from being extremely alert to having very low alertness. In the FSS, subjects are asked to rate their level of agreement or disagreement with statements relating to the level of subjective fatigue on a 7-point likert scale ranging from 1 (strongly disagree) to 7 (strongly agree). The SSS, FSS and AS take about 10 minutes to complete in total and each of the questionnaires have multiple questions or items that can be objectively used to evaluate the state measures. All the questionnaires have been previously validated by independent studies.

Some people may have higher sleep propensity than others, hence sleep disorder people will be quickly screened using the Epworth Sleepiness Scale (ESS)[71]. The ESS determines trait sleepiness and is an 8-item trait scale that assesses the subject's subjective likelihood of falling asleep in several soporific conditions. The scale refers to the subject's usual way of life in recent times. The ESS will be administered during the initial screening process.

The same level of alertness, subjective sleepiness and fatigue is expected in subjects using the experimental filters as in subjects exposed to unfiltered bright light. However, subjects using the mock filters will also show the same level of alertness, sleepiness and fatigue as those exposed to unfiltered lighting due to the lack of any filtering properties of the mock goggles. Subjects kept in darkness will show the highest level of sleepiness, fatigue and lowest levels of alertness.

Upon completion of the study, the filters are expected to be found to be effective in preventing melatonin suppression and reducing stress levels in response to nocturnal bright light exposure. The filters are expected to normalize melatonin and cortisol levels to at least 60%, and possibly 80% or more, of physiologic levels. Upon fulfillment of these criteria, a clinical trial will be performed with active rotating shift workers. The long term effectiveness of these filters in preventing phase shifts observed with bright light exposure will also be investigated and objective evaluation of daytime sleep physiology and nighttime cognitive functioning and psychomotor performance in rotating night shift workers will be performed.

Since there are no invasive procedures in this study the potential risks involved are greatly reduced. The only possible risk factor is sleep deprivation and to avoid the problem of sleep deprivation and driving, subjects will be provided monetary compensation to take taxis back home. In addition, studies will not be performed on consecutive nights to allow for normal sleep on at least 2 nights between each study session.

For the primary endpoint, a two-sided alternative hypothesis at the $\alpha=0.05$ level with a sample size of 25 subjects will yield 70.5% power to detect a standardized difference of 0.50 and 84% power to detect a standardized difference of 0.60. A "standardized difference" is defined as $\Delta/\sigma$, where the difference of interest is $\Delta$ and the standard deviation of the difference is $\sigma$. The sample should be increased to accommodate a minimum dropout rate of 17%. Thus, 30 patients will be recruited for the study.

Results from the four different conditions will be analysed using the General Linear Model Procedure and Multifactor analysis of Variance (MANOVA) to detect statistically significant differences in hormone levels. Further analysis will include Tukey post hoc paired comparisons. Non-parametric Mann-Whitney's U-test will be used for assessment of the subjective scales. The relationship between melatonin levels and subjective sleepiness, fatigue and alertness will be analyzed using Spearman correlations. Statistical analysis will be performed using SPSS software for Windows.

EXAMPLE 4

Figure 9:
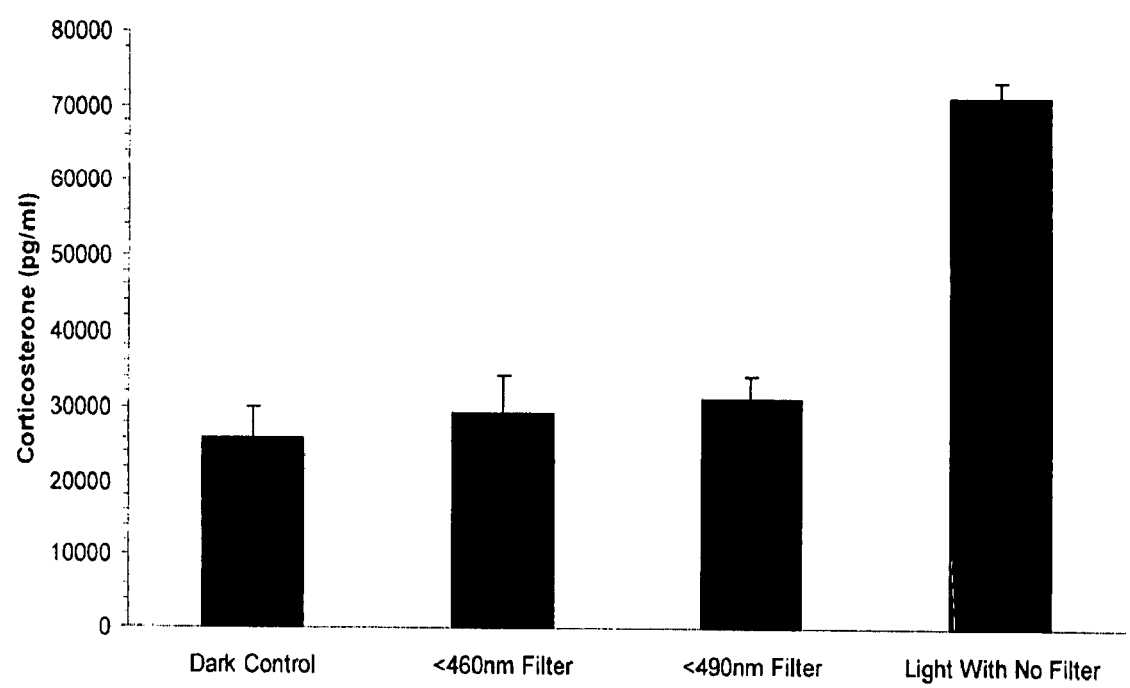
FIG. 9 shows corticosterone levels at 12 am in an animal model under lighted conditions with no filter, with a filter that substantially blocks wavelengths below 460 nm, with a filter that substantially blocks wavelengths below 490 nm and under no light condition.
Figure 10:
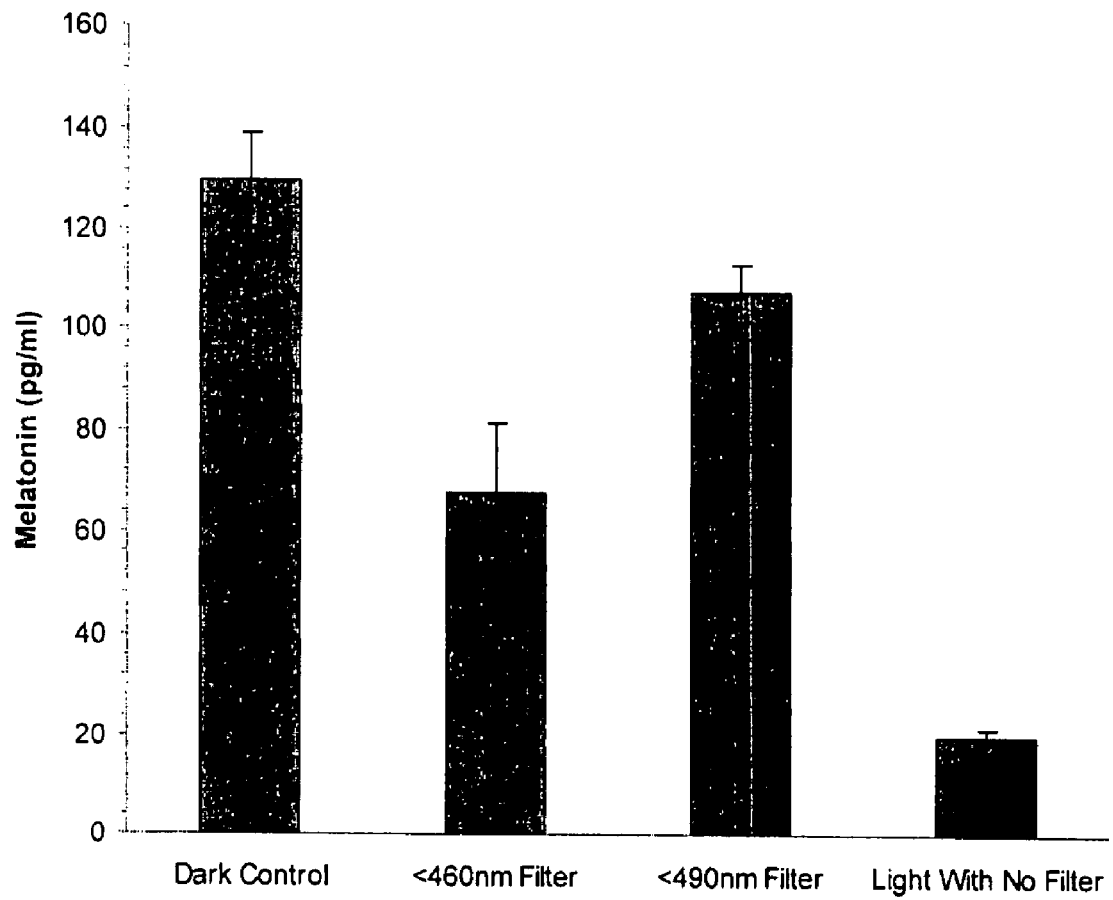
FIG. 10 shows melatonin levels at 12 am in an animal model under lighted conditions with no filter, with a filter that substantially blocks wavelengths below 460 nm, with a filter that substantially blocks wavelengths below 490 nm and under no light condition.

The same methodology was employed as in Example 1, but the notch filters were replaced with the filters whose transmission profiles are shown in Tables 1 and 2 above, i.e. a filter that substantially blocks wavelengths of light below about 460 nm and a filter that substantially blocks wavelengths of light below about 490 nm. As shown in FIG. 9, filtering these wavelengths of light normalizes glucocorticoid secretion to physiologic levels. As shown in FIG. 10, at 12 am, both lenses normalized melatonin levels. While the lens that blocks wavelengths of light below 490 nm results in melatonin levels more closely approaching that of the dark control, the 460 nm filter does preserve up to 53% of the dark control values.

Figure 11:
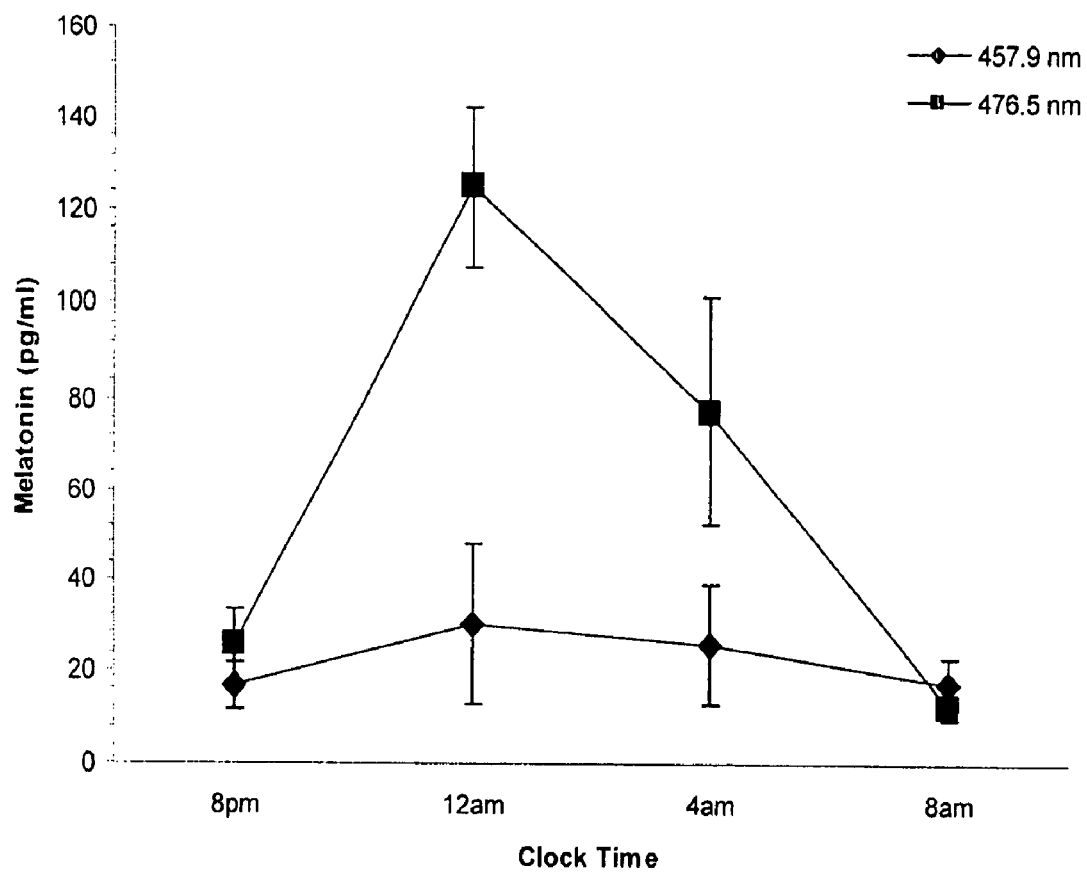
FIG. 11 shows the melatonin profile in an animal model over 12 hours from 8 pm to 8 am with a 457.9 nm notch filter and a 476.5 nm notch filter.

Notch filter data from Example 1 is shown in FIG. 11 for comparison purposes. As illustrated, the notch filter of 452-462 nm is not effective in increasing melatonin levels, although the 460 nm filter of Table 1 is effective. This is likely due to the broader range of the 460 nm filter, which also blocks a significant percentage of wavelengths at 470 nm.

While this invention has been described with reference to illustrative embodiments and examples, the description is not intended to be construed in a limiting sense. Thus, various modifications will be apparent to persons skilled in the art upon reference to this description.

Further, elements illustrated or described in connection with one exemplary embodiment may be combined with the features of other embodiments. Such modifications and variations are intended to be included within the scope of the present invention.

All publications, patents and patent applications referred to herein are incorporated by reference in their entirety to the same extent as if each individual publication, patent or patent application was specifically and individually indicated to be incorporated by reference in its entirety.

REFERENCES

1. Sunter D. Working Shift. Perspectives, Statistics Canada (Catalogue 75-001E), Spring 1993:16-23.
2. Van Dongen P A, Maislin G, Mullington J M, Dinges D F. The cumulative cost of additional wakefulness: dose-response effects on neurobehavioral functions and sleep physiology from chronic sleep restriction and total sleep deprivation. *Sleep* 2003 26: 117-126.
3. Mitler M M, Carskadon M A, Czeisler C A, Dement W C, Dinges D F, Graeber R C. Catastrophes, Sleep, and Public Policy: Consensus Report. *Sleep* 1988 11: 100-109.
4. Smith L, Folkard S, Poole C J. Increased injuries on night shift. *Lancet* 1994 344:1137-1139.
5. Luna T D. Air Traffic Controller Shiftwork: what are the implications for aviation safety? A review. *Aviat Space Environ Med* 1997 68:69-79.
6. Frank A L. Injuries related to shiftwork. *Am J Prev Med* 2000 18: 33-36.
7. Davis S, Mirick D K. Stevens R G. Night shift work, light at night, and risk of breast cancer. *J Natl Cancer Inst.* 2001 93: 1557-1562.
8. Schernhammer, E S Laden F, Speizer F E, Willett W C, Hunter D J, Kawachi I. Night-shift work and risk of colorectal cancer in the nurses' health study. *J Natl Cancer Inst.* 2003 95: 825-828.
9. Hansen J. Light at night, shiftwork, and breast cancer risk. *J Natl Cancer Inst.* 2001 93: 1513-1515.
10. Kubo T, Ozasa K, Mikami K, Wakai K, Fujino Y, Watanabe Y, et al., Prospective Cohort Study of the Risk of Prostate Cancer among Rotating-Shift Workers: Findings from the Japan Collaborative Cohort Study. *Am J Epidemiol* 2006 164: 549-555
11. Sookoian S, Gemma C, Gianotti T F, Burgueño A, Alvarez A, González C D, Pirola C J. Effects of rotating shift work on biomarkers of metabolic syndrome and inflammation. *J Intern Med* 2007 261: 285-292.
12. Healy D, Waterhouse J M: The circadian system and affective disorders: clocks or rhythms? *Chronobiol Intern* 1990 7: 5-9
13. Colligan M J, Rosa R R. Shiftwork: Effects of social and family life. Shiftwork: Occupational Medicine—*State of the Art Reviews* 1990 5(2): 315
14. Van Dongen H P. Shift work and inter-individual differences in sleep and sleepiness. *Chronobiol Int.* 2006 23:1139-47
15. Wood P A, Du-Quiton J, You S, Hrushesky W J. Circadian clock coordinates cancer cell cycle progression, thymidylate synthase, and 5-fluorouracil therapeutic index. *Mol Cancer Ther.* 2006 5: 2023-33.
16. Panda S, Antoch M P, Miller B H, Ai S, Schook A B, Staume M, et al. Coordinated transcription of key pathways in the mouse by the circadian clock. *Cell* 2002 109: 307-320
17. Richter H G, Torres-Farfan C, Rojas-Garcia P P, Campino C, Torrealba F, Seron-Ferre M. The Circadian Timing System: Making Sense of day/night gene expression. 2004 *Biol Res* 37: 11-28
18. Shanahan T L, Zeitzer J M, Czeisler C A. Resetting the melatonin rhythm with light in humans. *J Biol Rhythms* 1997 12:556-67.
19. Whitmore J N, French J, Fischer J R. Psychophysiological effects of a brief nocturnal light exposure. *J Hum Ergol.* 2001 30: 267-72.
20. Kubota T, Uchiyama M, Suzuki H, Shibui K, Kim K, Tan X, et al. Effects of nocturnal bright light on saliva melatonin, core body temperature and sleep propensity rhythms in human subjects. *Neurosci Res.* 2002 42: 115-22.
21. Czeisler C A, Kronauer R E, Allan J S, Duffy J F, Jewett M E, Brown E N, et al. Bright light induction of strong (type 0) resetting of the human circadian pacemaker. *Science* 1989 244: 1328-1333.
22. Zeitzer J M, Dijk D J, Kronauer R, Brown E, Czeisler C. Sensitivity of the human circadian pacemaker to nocturnal light: melatonin phase resetting and suppression. *J Physiol.* 2002 526: 695-702.
23. Khalsa S B, Jewett M E, Cajochen C, Czeisler C A. A phase response curve to single bright light pulses in human subjects. *J Physiol.* 2003 549: 945-952.
24. Benloucif S, Masana M I, Yun K, Dubocovich M L. Interactions between light and melatonin on the circadian clock of mice. *J Biol Rhythms.* 1999 14: 281-9.
25. Benshoff H M, Brainard G C, Rollag M D, Lynch G R. Suppression of pineal melatonin in Peromyscus leucopus by different monochromatic wavelengths of visible and near-ultraviolet light (UV-A). *Brain Res.* 1987 420: 397-402.
26. Hattar S, Lucas R J, Mrosovsky N, Thompson S, Douglas R H, Hankins M W, Lemk J, Biel M, Hofmann F, Foster R G, Yau K W. Melanopsin and rod-cone photoreceptive systems account for all major accessory visual functions in mice. *Nature* 2003 424: 76-81
27. Thapan K, Adrendt J, Skene D J. An action spectrum for melatonin suppression: evidence for a novel non-rod, non-cone photoreceptor system in humans. *J Physiol* 2001 535: 261-7.
28. Barrenetxe J, Delagrange P, Martinez J A. Physiological and metabolic functions of melatonin. *J Physiol Biochem.* 2004 60: 61-72
29. Blask D E, Dauchy R T, Sauer L A, Krause J A, Brainard G C. Growth and fatty acid metabolism of human breast cancer (MCF-7) xenografts in nude rats: impact of constant light-induced nocturnal melatonin suppression. *Breast Cancer Res Treat.* 2003 79: 313-20.
30. Blask D E, Brainard G C, Dauchy R T, Hanifin J P, Davidson L K, Krause J A et al. Melatonin-depleted blood from premenopausal women exposed to light at night stimulates growth of human breast cancer xenografts in nude rats. *Cancer Res.* 2005 65: 11174-84.
31. Ishida A, Mutoh T, Ueyama T, Bando H, Masubuchi S, Nakahara D, et al. Light activates the adrenal gland: Timing of gene expression and glucocorticoid release. *Cell Metab.* 2005 2: 297-307 and Comment in: Cell Metab. November 2005; 2(5): 278-81.
32. Hammer F, Stewart P M. Cortisol metabolism in hypertension. *Best Pract Res Clin Endocrinol Metab.* 2006 20: 337-53
33. Steckler T, Holsboer F, Reul J M. Glucocorticoids and depression. *Baillieres Best Pract Res Clin Endocrinol Metab.* 1999 13: 597-614
34. Runnebaumand I B, Bruning A. Glucocorticoids Inhibit Cell Death in Ovarian Cancer and Up-regulate Caspase Inhibitor cIAP2 *Clin Cancer Res* 2005 11: 6325-6332
35. Schrey M P, Patel K V, Tezapsidis N. Bombesin and glucocorticoids stimulate human breast cancer cells to produce endothelin, a paracrine mitogen for breast stromal cells. *Cancer research* 1992 52: 1786-1790
36. Barker D. In utero programming of chronic disease. *Clin Sci* 95: 115-128, 1998.
37. Barker D J, Gluckman P D, Godfrey K M, Harding J E, Owens J A, and Robinson J S. Fetal nutrition and cardiovascular disease in adult life. *Lancet* 341: 938-941, 1993.
38. Edwards C R, Benediktsson R, Lindsay R S, and Seckl J R. Dysfunction of placental glucocorticoid barrier: a link between the fetal environment and adult hypertension? *Lancet* 341: 355-357, 1993.
39. Arai Y and Gorski R A. Critical exposure time for androgenization of the developing hypothalamus in the female rat. *Endocrinology* 82: 1010-1014, 1968.
40. Gustafsson J A, Mode A, Norstedt G, and Skett P. Sex steroid induced changes in hepatic enzymes. *Annu Rev Physiol* 45: 51-60, 1983.
41. Ward R M. Pharmacologic enhancement of fetal lung maturation. *Clin Perinatol* 21: 523-542, 1994.
42. Newnham J P, Evans S F, Godfrey M, Huang W, Ikegami M, and Jobe A. Maternal, but not fetal, administration of corticosteroids restricts fetal growth. *J Matern Fetal Med* 8: 81-87, 1999.
43. Reinisch J M, Simon N G, Karow W G, and Gandelman R. Prenatal exposure to prednisone in humans and animals retards intrauterine growth. *Science* 202: 436-438, 1978.
44. Goland R S, Jozak S, Warren W B, Conwell I M, Stark R I, and Tropper P J. Elevated levels of umbilical cord plasma corticotropin-releasing hormone in growth-retarded fetuses. *J Clin Endocrinol Metab* 77: 1174-1179, 1993.
45. Benediktsson R, Lindsay R S, Noble J, Seckl J R, and Edwards C R. Glucocorticoid exposure in utero: new model for adult hypertension. *Lancet* 341: 339-341, 1993.
46. Lindsay R S, Lindsay R M, Edwards C R, and Seckl J R. Inhibition of 11-beta-hydroxysteroid dehydrogenase in pregnant rats and the programming of blood pressure in the offspring. *Hypertension* 27: 1200-1204, 1996.
47. Lindsay R S, Lindsay R M, Waddell B J, and Seckl J R. Prenatal glucocorticoid exposure leads to offspring hyperglycaemia in the rat: studies with the 11 β-hydroxysteroid dehydrogenase inhibitor carbenoxolone. *Diabetologia* 39: 1299-1305, 1996.
48. Nyirenda M J, Lindsay R S, Kenyon C J, Burchell A, and Seckl J R. Glucocorticoid exposure in late gestation permanently programs rat hepatic phosphoenolpyruvate carboxykinase and glucocorticoid receptor expression and causes glucose intolerance in adult offspring. *J Clin Invest* 15: 2174-2181, 1998.
49. Shirayama M, Shirayama Y, Iida H, et al. The psychological aspects of patients with delayed sleep phase syndrome (DSPS). *Sleep Med.* 2003;4(5):427-433.
50. Wetterberg L. Clinical importance of Melatonin. *Prog Brain Res.* 1979;52:539-4
51. Wetterberg L. Chapter 3. In: Shaffi M, Shaffi S L, eds. *Melatonin in adult depression.* Washinton DC, MD: American Psychiatric Press Inc.; 1998, 43-79.
52. Tuunainen A, Kripe D F, Elliott J A, Assmus J D, Rex K M. Depression and endogenous melatonin in post menopausal women. *J Affect Disord.* 2002;69(1-3):149-58.
53. Okawa M, Uchiyama M, Ozaki S, Shibui K, Ichikawa H. Circadian rhythm sleep disorders in adolescents: clinical trials of combined treatments based on chronobiology. Psychiatry Clin Neurosci. 1998;52:483-490.
54. Owens J. Insomnia in Children and Adolescents. *Journal of Clinical Sleep Medicine,* 2005 1: 454-e458
55. Wolfson A R, Carskadon M A. Early school start times affect sleep and daytime functioning in adolescents. Sleep Research 1996; 25: 117.
56. Wolfson A R, Carskadon M A. Sleep schedules and daytime functioning in adolescents. Child Dev 1998 August; 69: 875-887.
57. Gibson E S, Powles A C P, Chilcott L, Carll D, O'Brien S, Ogilvie R, Trajanovic N, Sirianni D, Shapiro C. The Impact of "Sleepiness" on Adolescent Students. Report of Population Health Grant 5555-15-1997-0000051, Health Canada, 1998-2002.
58. Akerstedt T, Ficca G. Alertness-enhancing drugs as a countermeasure to fatigue in irregular work hours. *Chronobiol Int* 1997 14: 145-158.
59. Rosa R R, Bonnet M H, Bootzin R R, Eastman C I, Monk T, Penn P E. Intervention factors for promoting adjustment to nightwork and shiftwork. *Occup Med* 1995 5: 391-414.
60. Czeisler C A, Johnson M P, Duffy J F, Brown E N, Ronda J M, Kronauer R E. Exposure to bright light and darkness to treat physiologic maladaptation to night work. *N Engl J Med* 1990 322: 1253-1259.
61. Dawson D, Campbell S S. Timed exposure to bright light improves sleep and alertness during simulated night shifts. *Sleep* 1991 14: 511-516.
62. Horowitz T S, Cade B E, Wolfe J M, Czeisler C A. Efficacy of bright light and sleep/darkness scheduling in alleviating circadian maladaptation to night work. *Am J Physiol Endocrinol Metab* 2001 281: E384-E391.
63. Cajochen C, Munch M, Kobialka S, Kräuchi K, Steiner R, Oelhafen P, Orgül S and Wirz-Justice A. High Sensitivity of Human Melatonin, Alertness, Thermoregulation, and Heart Rate to Short Wavelength Light. *J Clin Endocrinol Metab.* 2005 90(3): 1311-1316.
64. Revell V, Arendt J, Fogg L and Skene D. Alerting effects of light are sensitive to very short wavelengths. *Neuroscience Letters.* 2006 399: 96-100.
65. Kayumov L, Casper R F, Hawa R J, Perelman B, Chung S A, Sokalsky S and Shapiro C M. Blocking Low-Wavelength Light Prevents Nocturnal Melatonin Suppression with No Adverse Effect on Performance during Simulated Shift Work. *J Clin Endocrinol Metab.* 2005 90: 2755-61.
66. Kayumov L, Zhdanova I V, Shapiro C M. Melatonin, sleep, and circadian rhythm disorders. *Semin Clin Neuropsychiatry.* 2000 5: 44-55.
67. Wirz-Justice A. Biological rhythm disturbances in mood disorders. *Int Clin Psychopharmacol.* 2006 21 Suppl 1: S11-5.
68. Hoddes E, Zarcone V, Smythe H. Quantification of sleepiness: A new approach. *Psychophysiol* 1973 10:431-436.

69. Krupp L B, LaRocca N G, Muir-Nash J. Steinberg A D. The fatigue severity scale. Application to patients with multiple sclerosis and systemic lupus erythematosus. *Arch. Neurol.* 1989 46: 1121-1123.
70. Kayumov L, Brown G, Jindal R, Buttoo K, Shapiro C M. A randomized, double-blind, placebo-controlled crossover study of the effect of exogenous melatonin on delayed sleep phase syndrome. Psychosom Med 2001;63:40-8.
71. Johns M W. A new method for measuring daytime sleepiness: the Epworth Sleepiness Scale. *Sleep* 1991; 14:540-5.

What is claimed is:

1. A method of maintaining the circadian rhythm of a subject exposed to light at night comprising selectively substantially blocking retinal exposure of the subject to light of wavelengths less than about 490 nm during the night, wherein selectively substantially blocking comprises transmitting less than 40 percent of the blocked wavelengths of light, while allowing transmission of more than 40 percent of non-blocked wavelengths of light and wherein the method inhibits melatonin suppression by light at night.

2. The method of claim 1, wherein the method of maintaining the circadian rhythm comprises normalizing levels of melatonin and at least one glucocorticoid in the subject.

3. The method of claim 2, comprising normalizing the levels of melatonin and cortisol in the subject.

4. The method of claim 1, wherein the subject is awake and in an artificially lighted environment.

5. The method of claim 4, wherein the subject has Delayed Sleep Phase Syndrome.

6. The method of claim 5, wherein the subject is an adolescent.

7. The method of claim 4, wherein the method is practised throughout the night.

8. The method of claim 4, wherein the subject is a female.

9. The method of claim 4, wherein the subject is pregnant.

10. The method of claim 4, wherein substantial blocking of wavelengths of light is by means of an optical filter.

11. The method of claim 10, wherein the optical filter is incorporated into eyewear.

12. The method of claim 10, wherein the optical filter is incorporated into a light cover.

13. The method of claim 10, wherein the optical filter is incorporated into a coating for a light source.

14. The method of claim 10, wherein the optical filter is incorporated into a light source.

15. The method of claim 4, wherein the light source excludes the blocked wavelengths of light.

16. The method of claim 1, wherein selectively substantially blocking comprises transmitting less than 40 percent, less than 30 percent, less than 20 percent or less than 10 percent of the blocked wavelengths of light, while allowing transmission of more than 50 percent, 60 percent, 70 percent, 80 percent, 90 percent or 100 percent of non-blocked wavelengths of light.

17. A method of maintaining the circadian rhythm of a subject exposed to light at night comprising selectively substantially blocking retinal exposure of the subject to light of wavelengths less than about 480 nm during the night, wherein selectively substantially blocking comprises transmitting less than 40 percent of the blocked wavelengths of light, while allowing transmission of more than 40 percent of non-blocked wavelengths of light and wherein the method inhibits melatonin suppression by light at night.

18. The method of claim 17, wherein the method of maintaining the circadian rhythm comprises normalizing levels of melatonin and at least one glucocorticoid in the subject.

19. The method of claim 18, comprising normalizing the levels of melatonin and cortisol in the subject.

20. The method of claim 17, wherein the subject is awake and in an artificially lighted environment.

21. The method of claim 20, wherein the subject has Delayed Sleep Phase Syndrome.

22. The method of claim 21, wherein the subject is an adolescent.

23. The method of claim 20, wherein the method is practised throughout the night.

24. The method of claim 20, wherein the subject is a female.

25. The method of claim 20, wherein the subject is pregnant.

26. The method of claim 20, wherein substantial blocking of wavelengths of light is by means of an optical filter.

27. The method of claim 26, wherein the optical filter is incorporated into eyewear.

28. The method of claim 26, wherein the optical filter is incorporated into a light cover.

29. The method of claim 26, wherein the optical filter is incorporated into a coating for a light source.

30. The method of claim 26, wherein the optical filter is incorporated into a light source.

31. The method of claim 20, wherein the light source excludes the blocked wavelengths of light.

32. The method of claim 17, wherein selectively substantially blocking comprises transmitting less than 40 percent, less than 30 percent, less than 20 percent or less than 10 percent of the blocked wavelengths of light, while allowing transmission of more than 50 percent, more than 60 percent, more than 70 percent, more than 80 percent, more than 90 percent or 100 percent of non-blocked wavelengths of light.

33. A method of maintaining the circadian rhythm of a subject exposed to light at night comprising selectively substantially blocking retinal exposure of the subject to light of wavelengths less than about 470 nm during the night, wherein selectively substantially blocking comprises transmitting less than 40 percent of the blocked wavelengths of light, while allowing transmission of more than 40 percent of non-blocked wavelengths of light and wherein the method inhibits melatonin suppression by light at night.

34. The method of claim 33, wherein the method of maintaining the circadian rhythm comprises normalizing levels of melatonin and at least one glucocorticoid in the subject.

35. The method of claim 34, comprising normalizing the levels of melatonin and cortisol in the subject.

36. The method of claim 33, wherein the subject is awake and in an artificially lighted environment.

37. The method of claim 36, wherein the subject has Delayed Sleep Phase Syndrome.

38. The method of claim 37, wherein the subject is an adolescent.

39. The method of claim 36, wherein the method is practised throughout the night.

40. The method of claim 36, wherein the subject is a female.

41. The method of claim 36, wherein the subject is pregnant.

42. The method of claim 36, wherein substantial blocking of wavelengths of light is by means of an optical filter.

43. The method of claim 42, wherein the optical filter is incorporated into eyewear.

44. The method of claim 42, wherein the optical filter is incorporated into a light cover.

45. The method of claim 42, wherein the optical filter is incorporated into a coating for a light source.

46. The method of claim 42, wherein the optical filter is incorporated into a light source.

47. The method of claim 36, wherein the light source excludes the blocked wavelengths of light.

48. The method of claim 33, wherein selectively substantially blocking comprises transmitting less than 40 percent, less than 30 percent, less than 20 percent or less than 10 percent of the blocked wavelengths of light, while allowing transmission of more than 50 percent, more than 60 percent, more than 70 percent, more than 80 percent, more than 90 percent or 100 percent of non-blocked wavelengths of light.

49. A method of maintaining the circadian rhythm of a subject exposed to light at night comprising selectively substantially blocking retinal exposure of the subject to light of wavelengths less than about 460 nm during the night, wherein selectively substantially blocking comprises transmitting less than 40 percent of the blocked wavelengths of light, while allowing transmission of more than 40 percent of non-blocked wavelengths of light and wherein the method inhibits melatonin suppression by light at night.

50. The method of claim 49, wherein the method of maintaining the circadian rhythm comprises normalizing levels of melatonin and at least one glucocorticoid in the subject.

51. The method of claim 50, comprising normalizing the levels of melatonin and cortisol in the subject.

52. The method of claim 49, wherein the subject is awake and in an artificially lighted environment.

53. The method of claim 52, wherein the subject has Delayed Sleep Phase Syndrome.

54. The method of claim 53, wherein the subject is an adolescent.

55. The method of claim 52, wherein the method is practised throughout the night.

56. The method of claim 52, wherein the subject is a female.

57. The method of claim 52, wherein the subject is pregnant.

58. The method of claim 52, wherein substantial blocking of wavelengths of light is by means of an optical filter.

59. The method of claim 58, wherein the optical filter is incorporated into eyewear.

60. The method of claim 58, wherein the optical filter is incorporated into a light cover.

61. The method of claim 58, wherein the optical filter is incorporated into a coating for a light source.

62. The method of claim 58, wherein the optical filter is incorporated into a light source.

63. The method of claim 52, wherein the light source excludes the blocked wavelengths of light.

64. The method of claim 49, wherein selectively substantially blocking comprises transmitting less than 40 percent, less than 30 percent, less than 20 percent or less than 10 percent of the blocked wavelengths of light, while allowing transmission of more than 50 percent, more than 60 percent, more than 70 percent, more than 80 percent, more than 90 percent or 100 percent of non-blocked wavelengths of light.

65. A method of normalizing levels of melatonin and at least one glucocorticoid in a subject exposed to light at night comprising selectively substantially blocking retinal exposure of the subject to light of wavelengths selected from the group consisting of between about 420 nm and about 490 nm; between about 430 nm and about 490 nm; between about 440 nm and about 490 nm; between about 420 nm and about 480 nm; between about 430 nm and about 480 nm; between about 440 nm and about 480 nm; between about 420 mm and about 470 nm; between about 430 nm and about 470 mm; between about 440 mm and about 470 mm; between about 420 mm and about 460 mm; between about 430 nm and about 460 nm; and between about 440 nm and about 460 mm; during the night, wherein selectively substantially blocking comprises transmitting less than 40 percent of the blocked wavelengths of light, while allowing transmission of more than 40 percent of non-blocked wavelengths of light and wherein the method inhibits melatonin suppression by light at night.

66. The method of claim 65, comprising normalizing the levels of melatonin and cortisol in the subject.

67. The method of claim 65, wherein selectively substantially blocking comprises transmitting less than 40 percent, less than 30 percent, less than 20 percent or less than 10 percent of the blocked wavelengths of light, while allowing transmission of more than 50 percent, more than 60 percent, more than 70 percent more than 80 percent, more than 90 percent or 100 percent of non-blocked wavelengths of light.

68. A device for maintaining the circadian rhythm of a subject exposed to light at night comprising an optical filter that selectively substantially blocks light of wavelengths Less than about 490 nm, wherein selectively substantially blocking comprises transmitting less than 40 percent of the blocked wavelengths of light, while allowing transmission of more than 40 percent of non-blocked wavelengths of light and wherein the device inhibits melatonin suppression by light at night.

69. The device of claim 68, wherein selectively substantially blocking comprises transmitting Less than 40 percent, less than 30 percent, less than 20 percent or less than 10 percent of the blocked wavelengths of light, while allowing transmission of more than 50 percent, more than 60 percent, more than 70 percent, more than 80 percent, more than 90 percent or 100 percent of non-blocked wavelengths of light.

70. A device for maintaining the circadian rhythm of a subject exposed to light at night comprising an optical filter that selectively substantially blocks light of wavelengths selected from the group consisting of between about 420 nm and about 490 nm; between about 430 nm and about 490 nm; between about 440 nm and about 490 nm; between about 420 nm and about 480 nm; between about 430 nm and about 480 nm; between about 440 nm and about 480 nm; between about 420 nm and about 470 nm; between about 430 nm and about 470 nm; between about 440 nm and about 470 nm; between about 420 nm and about 460 nm; between about 430 nm and about 460 nm; and between about 440 nm and about 460 nm, wherein selectively substantially blocking comprises transmitting less than 40 percent of the blocked wavelengths of light, while allowing transmission of more than 40 percent of non-blocked wavelengths of light and wherein the device inhibits melatonin suppression by light at night.

71. The device of claim 70, wherein selectively substantially blocking comprises transmitting less than 40 percent, less than 30 percent, less than 20 percent or less than 10 percent of the blocked wavelengths of light, while allowing transmission of more than 50 percent, more than 60 percent, more than 70 percent, more than 80 percent, more than 90 percent or 100 percent of non-blocked wavelengths of light.

* * * * *